United States Patent [19]
Yamaguchi et al.

[11] Patent Number: 5,818,527
[45] Date of Patent: Oct. 6, 1998

[54] IMAGE PROCESSOR FOR CORRECTING DISTORTION OF CENTRAL PORTION OF IMAGE AND PREVENTING MARGINAL PORTION OF THE IMAGE FROM PROTRUDING

[75] Inventors: Tatsuya Yamaguchi, Hino; Masaomi Tomizawa, Hachioji; Hiroyuki Watanabe, Yokohama; Mitsumasa Okada, Hachioji, all of Japan

[73] Assignee: Olympus Optical Co., Ltd., Tokyo, Japan

[21] Appl. No.: 574,639

[22] Filed: Dec. 19, 1995

[30] Foreign Application Priority Data

| Dec. 21, 1994 | [JP] | Japan | 6-318223 |
| Jan. 19, 1995 | [JP] | Japan | 7-006716 |
| Nov. 17, 1995 | [JP] | Japan | 7-299746 |

[51] Int. Cl.$^6$ .................................................. H04N 5/225
[52] U.S. Cl. ........................................ 348/335; 348/241
[58] Field of Search ................... 348/335, 241, 348/231, 340, 222; 382/293

[56] References Cited

U.S. PATENT DOCUMENTS 4,549,208 10/1985 Kamejima et al. ................. 348/149
5,005,957 4/1991 Kanamori et al. ................. 359/708
5,276,519 1/1994 Richards et al. .................. 348/335
5,489,940 2/1996 Richardson et al. ............... 348/335

FOREIGN PATENT DOCUMENTS

| 6-36020 | 2/1994 | Japan . |
| 07015647 | 1/1995 | Japan ................. H04N 5/232 |

*Primary Examiner*—Wendy Garber
*Attorney, Agent, or Firm*—Armstrong, Westerman, Hattori, McLeland & Naughton

[57] ABSTRACT

A distorted optical image formed on an image pickup surface by an optical system is photoelectrically converted by an image pickup device and written in memory cells of an image memory designated by write addresses. When the optical image is read, the image quality at the central portion is improved and the image is prevented from missing at the marginal portion so that the image can preferably be observed by correcting the distortion of an image in the area at the central side of the image pickup surface due to the optical system by read addresses obtained by converting the write addresses and preventing an image in the area at the marginal side from protrusion.

40 Claims, 29 Drawing Sheets

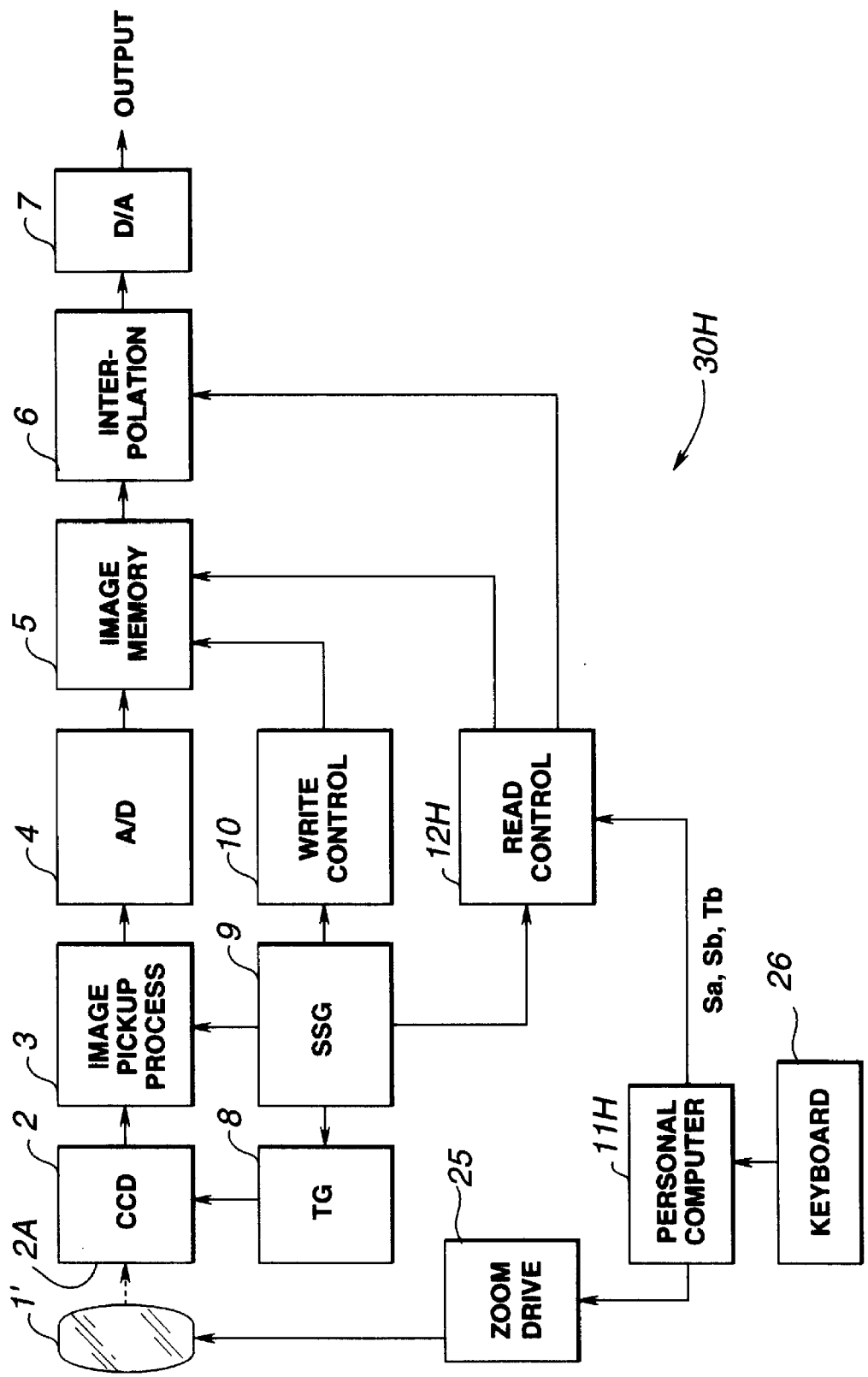

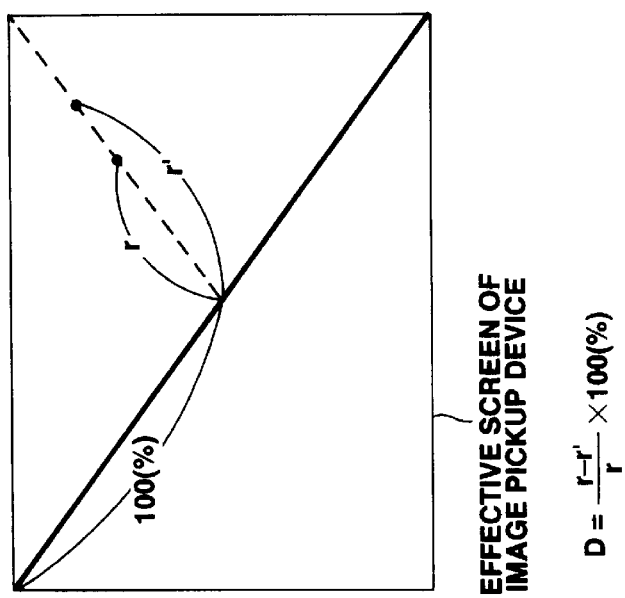
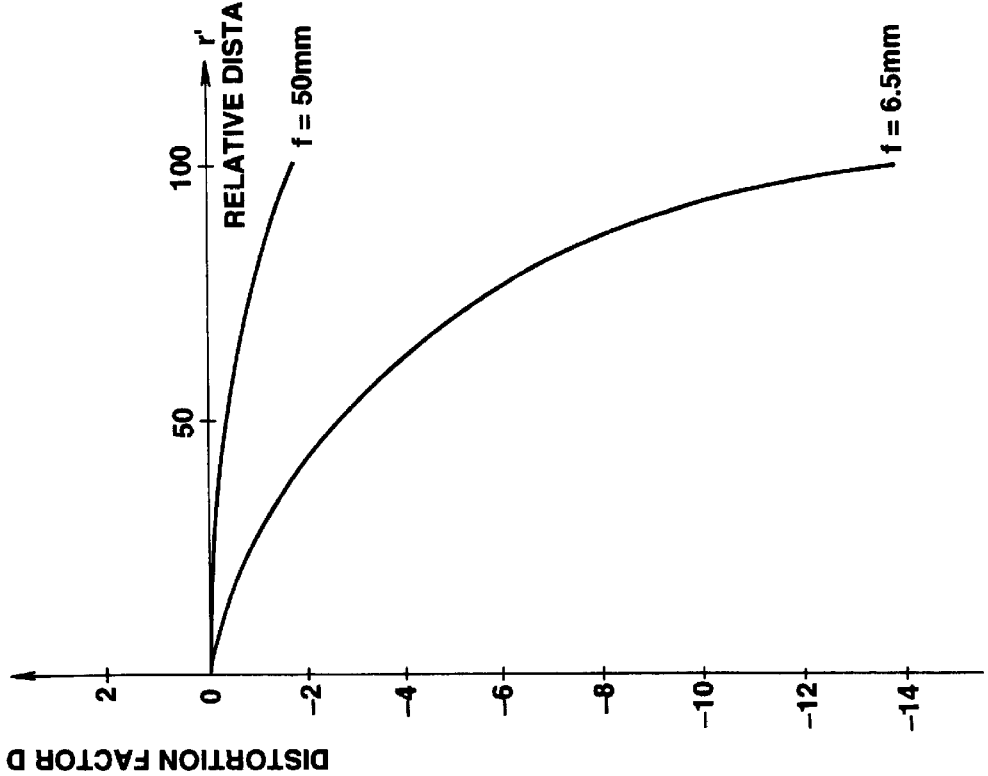

FIG.24
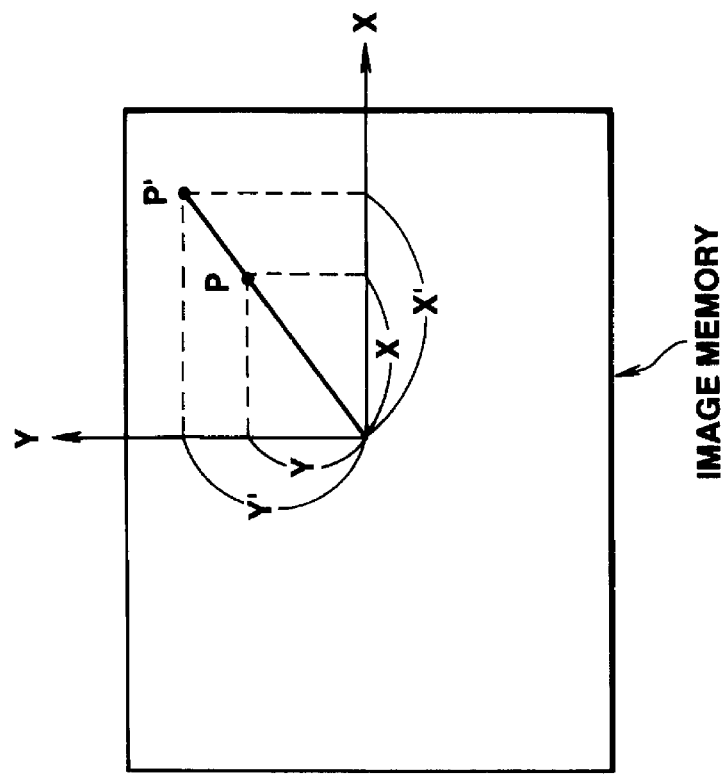
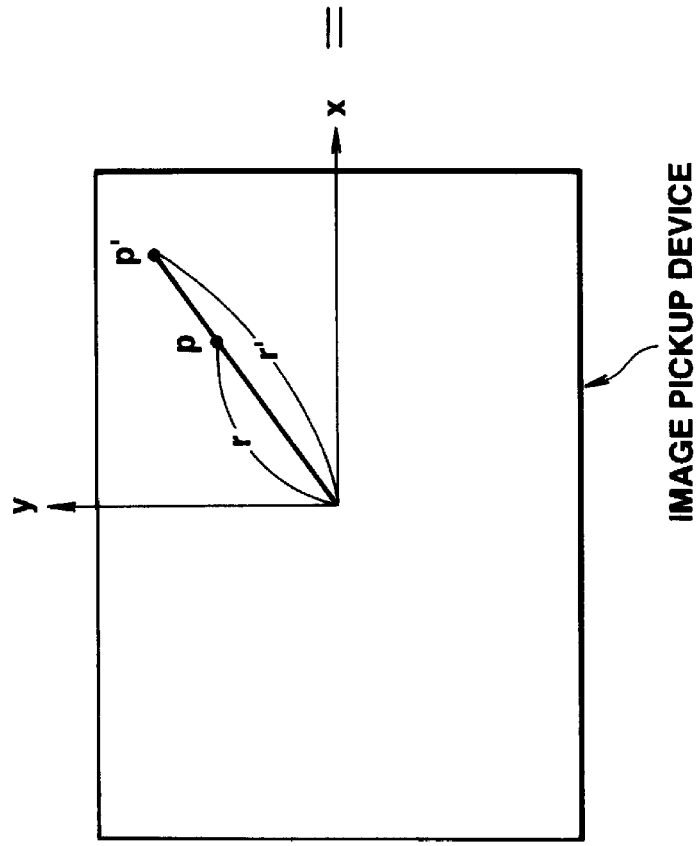

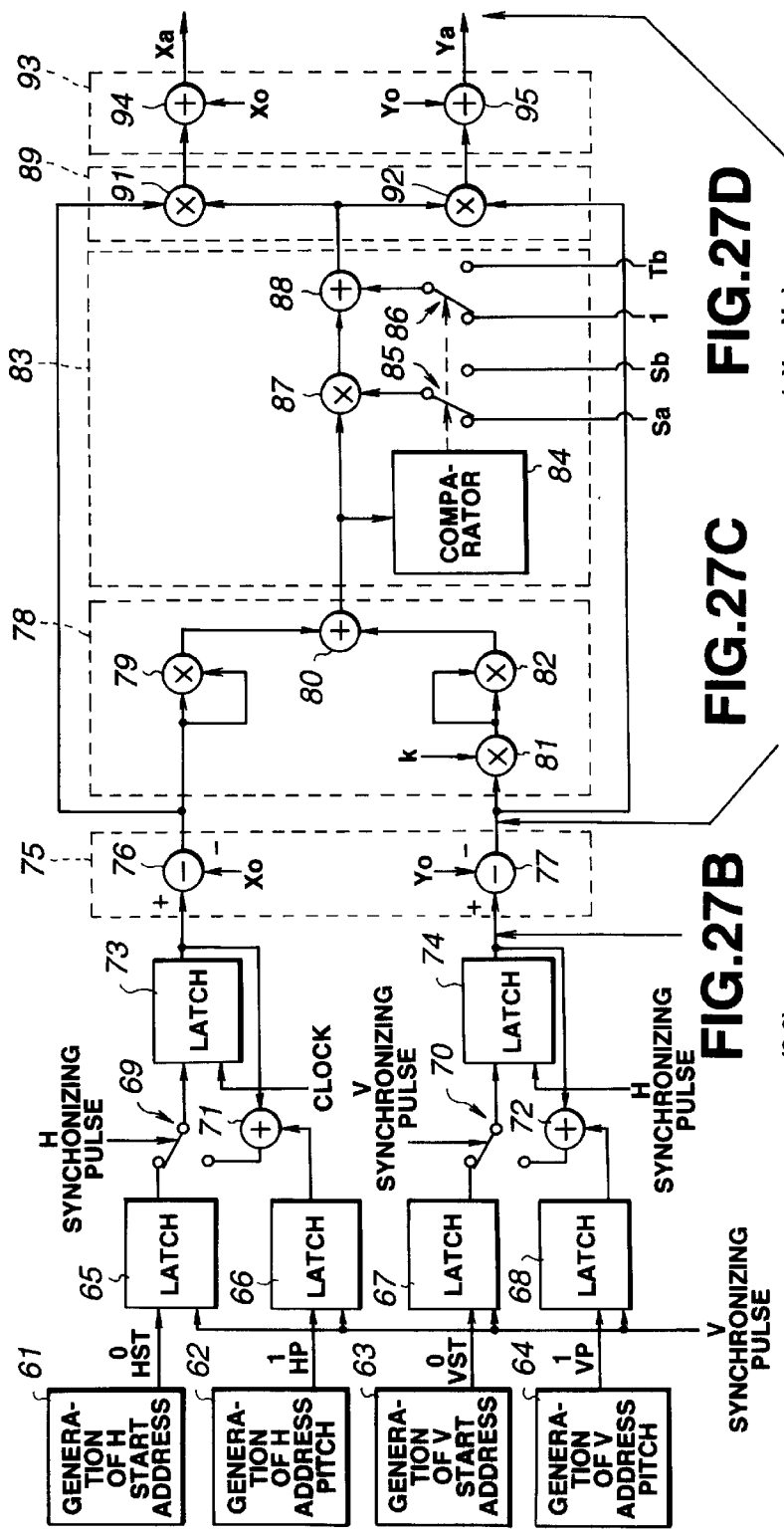

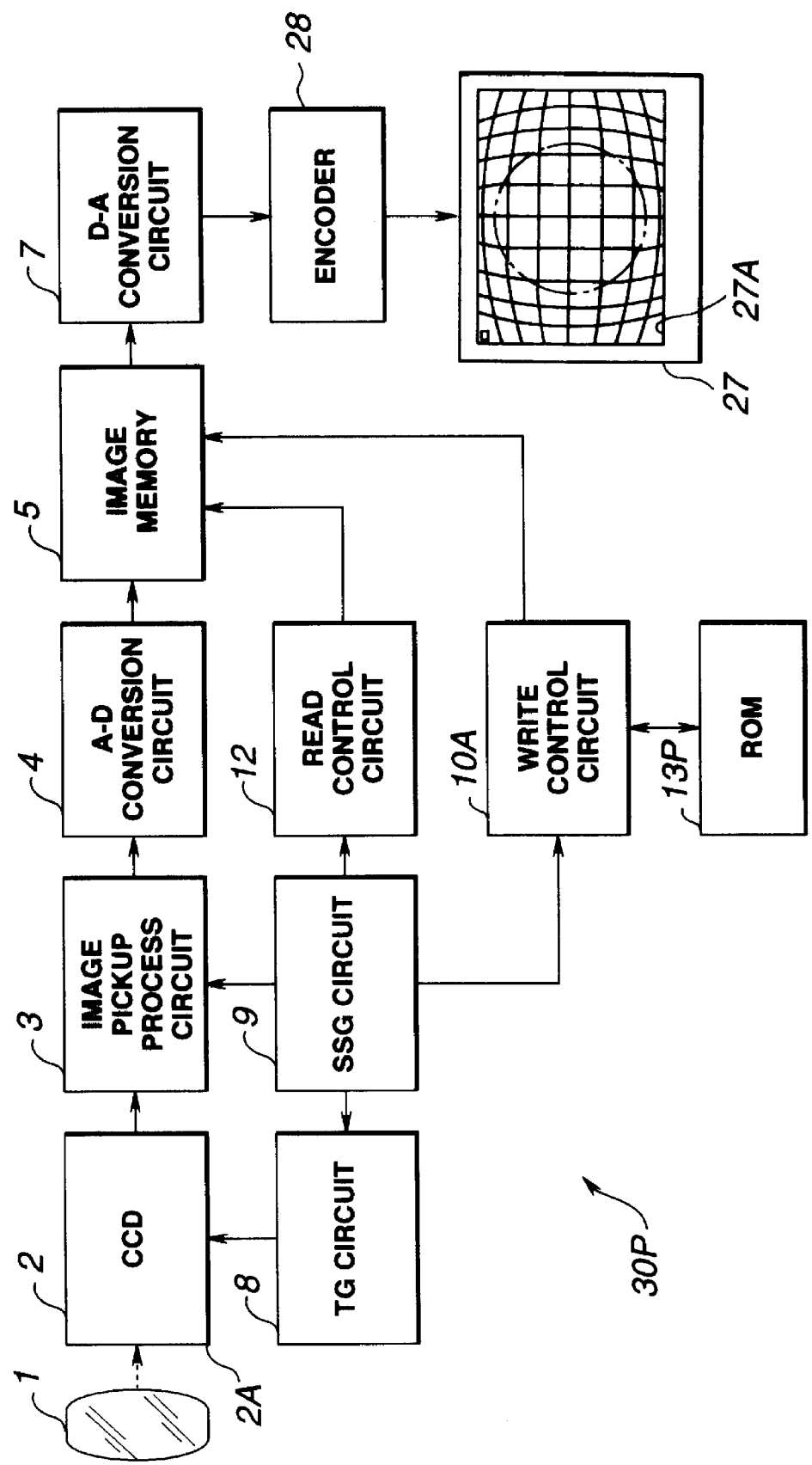

IMAGE PROCESSOR FOR CORRECTING DISTORTION OF CENTRAL PORTION OF IMAGE AND PREVENTING MARGINAL PORTION OF THE IMAGE FROM PROTRUDING

BACKGROUND OF THE INVENTION

1. Field of the Invention

The present invention relates to an image processor for correcting distortion of the central portion of an image captured by an optical system and preventing the marginal portion of the image from protruding.

2. Description of the Related Art

In the case of a conventional image processor for capturing image information of an object through an image pickup device, optical distortion occurs in the optical image of the object formed on the image pickup device through an optical lens and as a result, image data whose picture signal also has a distortion is captured.

The aforementioned optical distortion includes the "barrel distortion" shown in FIG. 1 and the "pin-cushion distortion" shown in FIG. 2. These distortions are distortions in which the image 101 or image 103 which should originally be present at the position shown by a broken line becomes the image 102 or image 104 formed at the position shown by a continuous line, respectively.

To correct the distortion of a picture signal including the above optical distortion, the distortion has been corrected in an image memory in the prior art converting the picture signal into a digital signal, and then writing the digital signal in an image memory and reading it from the memory correspondingly to the distortion characteristic.

In FIG. 1, for example, unless there is any distortion due to an optical lens, a square grid-like image to be stored in an image memory like the image in the image area 101 shown by the broken line is stored in the image memory like the image area 102 shown by the continuous line due to an optical distortion. Therefore, to perform correction, when reading the pre-correction image data from the image memory, the pre-correction image data stored in the point Pa is read at the timing for reading the point PA, the uncorrected image data stored in the point Pb is read at the timing for reading the point PB, and the uncorrected image data stored in the point Pd is read at the timing for reading the point PD. Then, the image area 102 of the distorted image to be corrected shown by the continuous line is read as the image of the undistorted original grid-like image area 101 shown by the broken line and its optical distortion is corrected.

FIG. 3 is a block diagram showing the structure of an image processor 29 of the prior art for correcting such optical distortion. In the case of the processor 29, an object is first imaged on the image pickup surface or photosensitive surface of a CCD 2 serving as an image pickup device through an optical lens 1. The object image formed on the image pickup surface of the CCD 2 includes an optical distortion. The object image is photoelectrically converted into electrical signals by the CCD 2.

The electrical signals of the CCD 2 are provided with predetermined processing by an image pickup process circuit 3 and thereby, picture signals are generated and supplied to an A-D conversion circuit 4. The picture signals converted from analog to digital signals by the A-D conversion circuit 4 are stored in an image memory 5. Write and read of signals in and from the image memory 5 are controlled by a write control circuit 10 and a read control circuit 12A, respectively.

Moreover, an SSG (synchronizing-signal generation) circuit 9 generates a reference timing signal to supply the signal to a TG (timing generation) circuit 8 to be mentioned later, the image pickup process circuit 3, the write control circuit 10, and the read control circuit 12A. The TG circuit 8 transmits horizontal (H) and vertical (V) read timing signals from the SSG circuit 9 to the CCD 2.

Furthermore, corrected data predetermined for each portion of the image pickup surface of the CCD 2 or the image storage area of the image memory is stored in a correction ROM 13A. The data stored as the predetermined corrected value is, for example, a corrected-value address value for correcting an optical distortion determined in accordance with the relation between a position on the continuous line and a position on the broken line as shown in FIG. 1.

A signal read from the image memory 5 in accordance with a read signal output from the read control circuit 12A in order to correct an optical distortion is interpolated by an interpolation circuit 6 and thereafter, converted into an analog signal by a D-A conversion circuit 7 and output to the monitor side.

In general, to perform a surgical operation under endoscopic observation, an endoscope with a relatively narrow angle of view of approx. 70° is used. In the case of an open operation, it is the present situation that the operation is performed by confirming the ambient situation such as insertion and extraction of a forceps at a low resolution though an area such as an operating portion always of interest to an operating surgeon and observed at a high resolution is relatively narrow because of the property of human eyes.

However, to perform an operation by using an endoscope, the range which can be observed by the operating surgeon is only an endoscope image displayed on a monitor and therefore, only a picture with an angle of view of approx. 70°; which is relatively narrow, is obtained. Thus, though the capacity for observing the central portion is not inferior compared to the case of the open operation, it is impossible at all to confirm the ambient situation such as insertion and extraction of a forceps.

When increasing the angle of view of the endoscope, their is a problem in that the optical distortion is intensified and the central portion becomes small on the monitor. Moreover, when making the endoscope approach the operating portion in order to magnify the interest area of the central portion on the monitor, the marginal portion gets out of the field of view and thereby, the wide-angle function cannot be shown.

To solve the above problems by an optical system (lens), it is difficult to realize the wide-angle function unless the curvature of the lens (object glass) is actually made discontinuous because the curvature of the central portion of the lens is different from that of the marginal portion of it. Therefore, an obtained image may locally be overlapped or an invisible portion may be produced. Moreover, to prevent aberration fading, the lens system becomes very large. Therefore, when the optical system must be stored in the front end of a thin inserting portion like the endoscope, it can hardly be used.

FIG. 4 is an illustration showing the optical-distortion correction characteristic for correcting an image having the barrel optical distortion shown in FIG. 5, which is the relation between undistorted imaged relative distance (%), that is, the relative distance (%) from the optical axis center O to be imaged under an optically-undistorted state and actually imaged relative distance (%), that is, the relative distance from the optical axis center O on an uncorrected image area formed by actually receiving an optical distortion. In this case, the relative distance (%) from the optical axis center O is shown in terms of the percentage of the relative distance between the optical center and a purposed position when assuming that half the length of the diagonal line of the image pickup surface of the CCD serving as an image pickup device is 100% as shown in FIG. 5.

From the characteristic example in FIG. 4, it is found that the undistorted image to be formed at the relative distance of 100% is actually formed at the relative distance of 80% shown by the point Pe. Therefore, as a correction characteristic, the uncorrected image data at the relative distance of 80% is output as corrected image data at the relative distance of 100% and the distortion in FIG. 5 is corrected by, for example, reading the uncorrected image portion stored at the relative distance of 80% at the timing for reading the relative distance of 100%.

FIG. 6 shows the relation between read timing for the above correction and data read position. The horizontal axis shows the image memory read timing by the relative distance (%) from the image center and the vertical axis shows the position for reading actual uncorrected image data by the relative distance (%) from the image center.

By correcting an optical distortion by the above correction method, a distorted image is corrected. However, in FIG. 6, an image stored in a relative distance range between 80 (%) and 100 (%) is not read but it is thrown up in the case of the prior art.

An image obtained by correcting the optically-distorted image 105 in FIG. 5 is shown as an example of the optical-distortion corrected image 107 in FIG. 7. From FIG. 7, it is found that an image "□" 106' which is the corrected image of the image "□" 106 formed at the left top of the point Pf of the image 105 to be corrected in FIG. 5 protrudes to the outside of the point PF located at an end of the image area on the corrected image 107. Points obtained by correcting the points Pe and Pf in FIG. 5 correspond to the points PE and PF at the ends of the image area in FIG. 7.

As described above, in the case of optical distortion correction performed by the prior art, the marginal portion of an image is not displayed after correction although the image is actually effectively formed on the image pickup surface of the CCD.

SUMMARY OF THE INVENTION

It is an object of the present invention to provide an image processor for performing image processing making it possible to display the central portion of a picked-up image at a high quality and the entire marginal portion of the image.

It is another object of the present invention to provide an image processor making it possible to obtain an image of a wide-angle view by a simple circuit.

The image processor of the present invention corrects an optical distortion of an image captured by an optical system by processing information and it is characterized by changing the above correction method for the central portion and the marginal portion of the image.

Another image processor of the present invention processes an image generated or inputted by the processor and has a characteristic that its processing becomes line-symmetric to the horizontal axis and/or vertical axis passing through the approximate center of the image. Moreover, the image processor has processing-information holding means necessary for processing corresponding to the characteristic related to at least one of the areas obtained by dividing the image vertically and/or horizontally and it is characterized by processing an image in accordance with the processing information held by the processing information means.

BRIEF DESCRIPTION OF THE DRAWINGS

FIGS. 8 to FIG. 15B show the first embodiment of the present invention, in which FIG. 8 is a block diagram showing the structure of an image processor of the first embodiment;

FIG. 11 is an illustration showing an undistorted grid line and a corrected line on a screen corresponding to an image output from the image processor in FIG. 8;

FIG. 12 is an illustration showing an optically-distorted grid line captured by an image pickup device and a corrected area in the case of the image processor in FIG. 8;

FIG. 13 is an illustration showing the entire structure of an endoscope system provided with a modification of the first embodiment;

FIG. 14 is an illustration showing the internal structure of each section in FIG. 13;

FIGS. 15A and 15B are an image to be corrected and an image corrected by an image processing unit;

FIG. 22 is a block diagram showing the structure of an image processor of the third embodiment of the present invention;

FIGS. 23A and 23B are illustrations showing the distortion factor to a relative distance when using a focal distance as a parameter and the definition of the distortion factor on an image pickup device;

FIG. 24 is an illustration showing the relation between the coordinate system on an image pickup device and the coordinate system on an image memory;

FIG. 27A is an illustration showing the concrete structure of a read control circuit;

FIGS. 27B to 27D are illustrations showing the coordinates at respective points;

FIG. 32 is a block diagram showing the structure of an image processor of the sixth embodiment;

DETAILED DESCRIPTION OF THE PREFERRED EMBODIMENTS

Embodiments of the present invention are described below by referring to the accompanying drawings.

Figure 8:
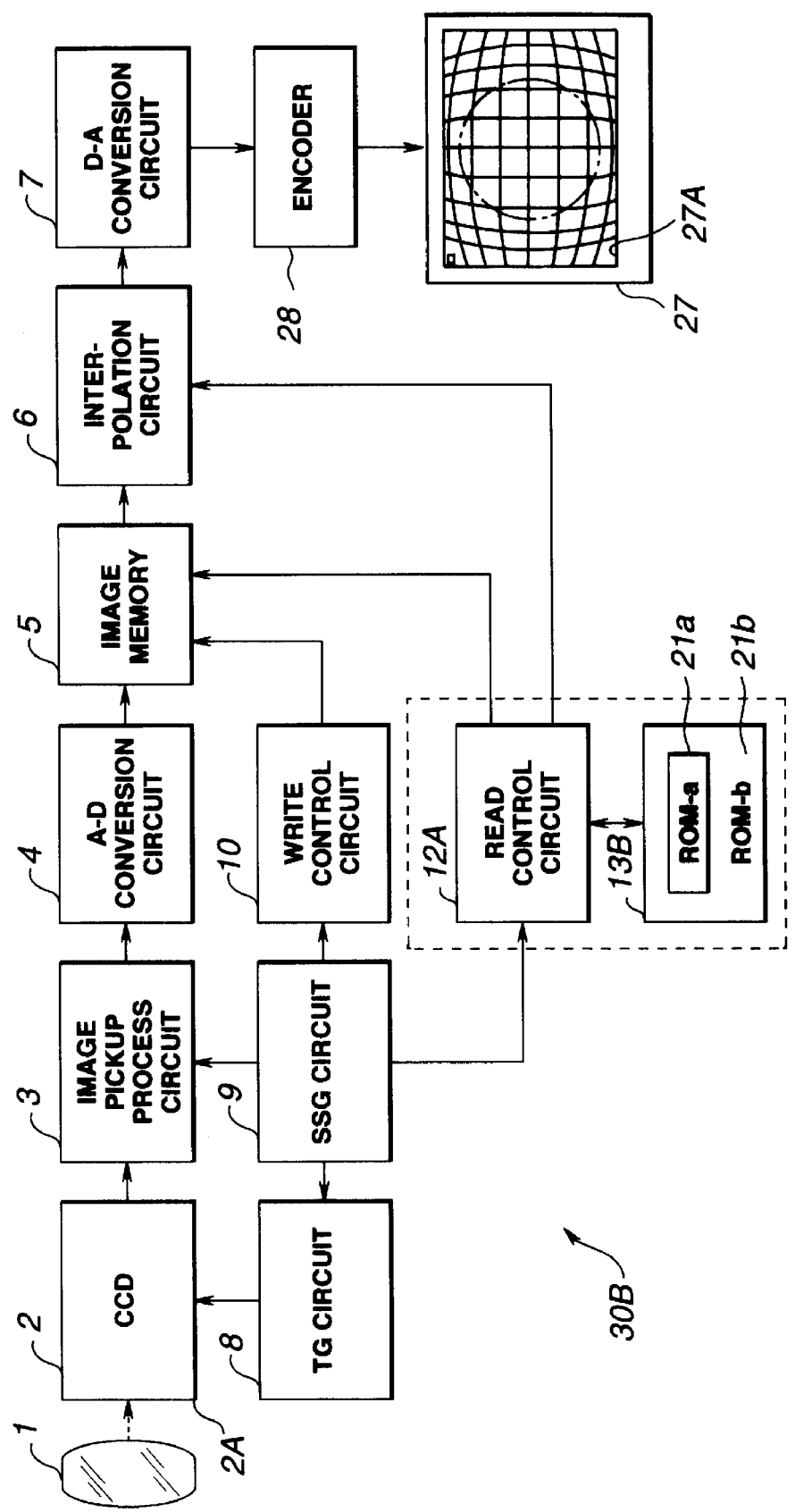

FIG. 8 is a block diagram showing the structure of an image processor 30B of the first embodiment of the present invention. The image processor 30B of this embodiment includes most of the same components as the structure of an image processor 29 of the prior art in FIG. 3 except a correction ROM 13B.

The ROM 13B functionally comprises a ROM_a21a for correcting the central area of an image and a ROM_b21b for correcting the marginal area outside of the central area.

In FIG. 8, an analog signal of a D-A conversion circuit 7 is converted into a standard picture signal by an NTSC encoder 28 and output to a monitor 27 to display a corrected image of, for example, a square-grid object imaged on an image pickup surface 2A of a CCD 2 by an optical lens 1 on a screen 27A of the monitor 27.

The display area of the screen 27A of the monitor 27 is set correspondingly to the image pickup surface 2A of the CCD 2 so that all images formed on the image pickup surface 2A of the CCD 2 can be displayed.

Figure 1:
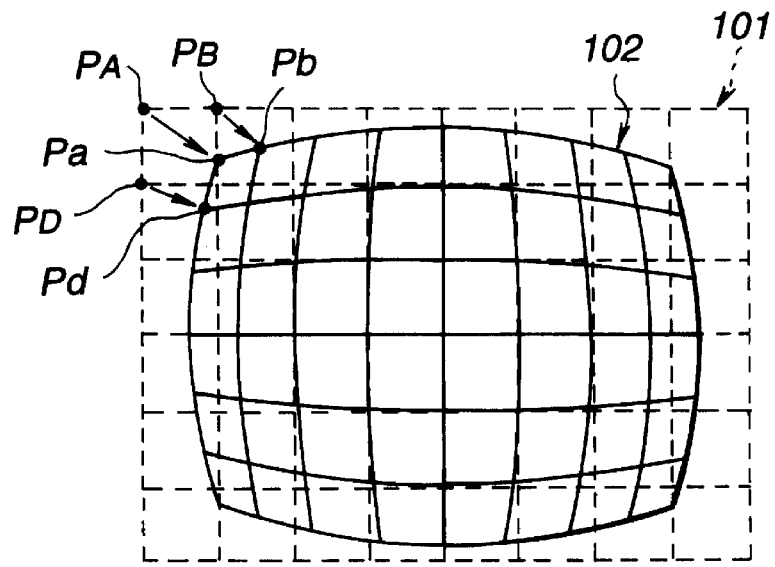
FIG. 1 is an illustration showing a barrel distortion among optical distortions of an image captured by an image pickup device.
Figure 2:
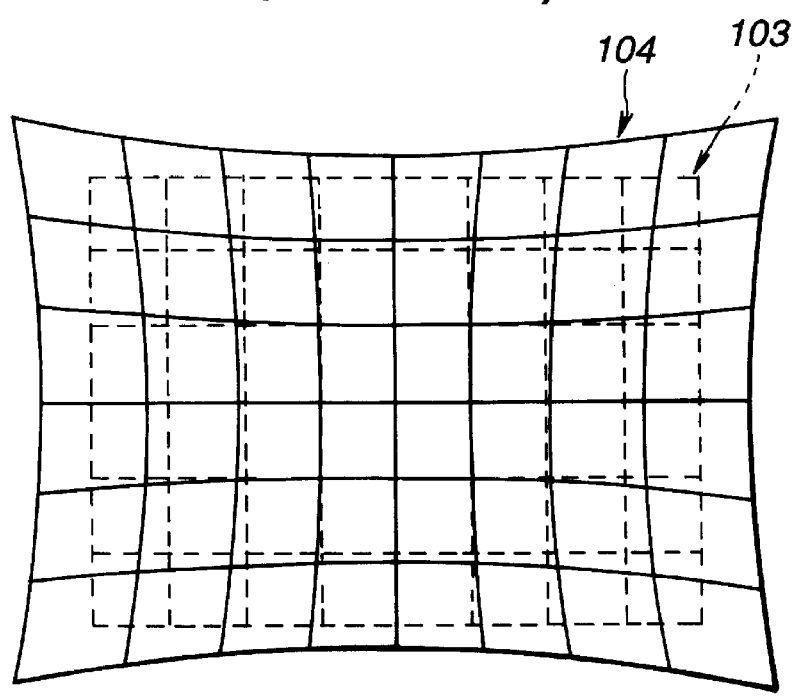
FIG. 2 is an illustration showing a pin-cushion distortion among optical distortions of an image captured by an image pickup device.
Figure 3:
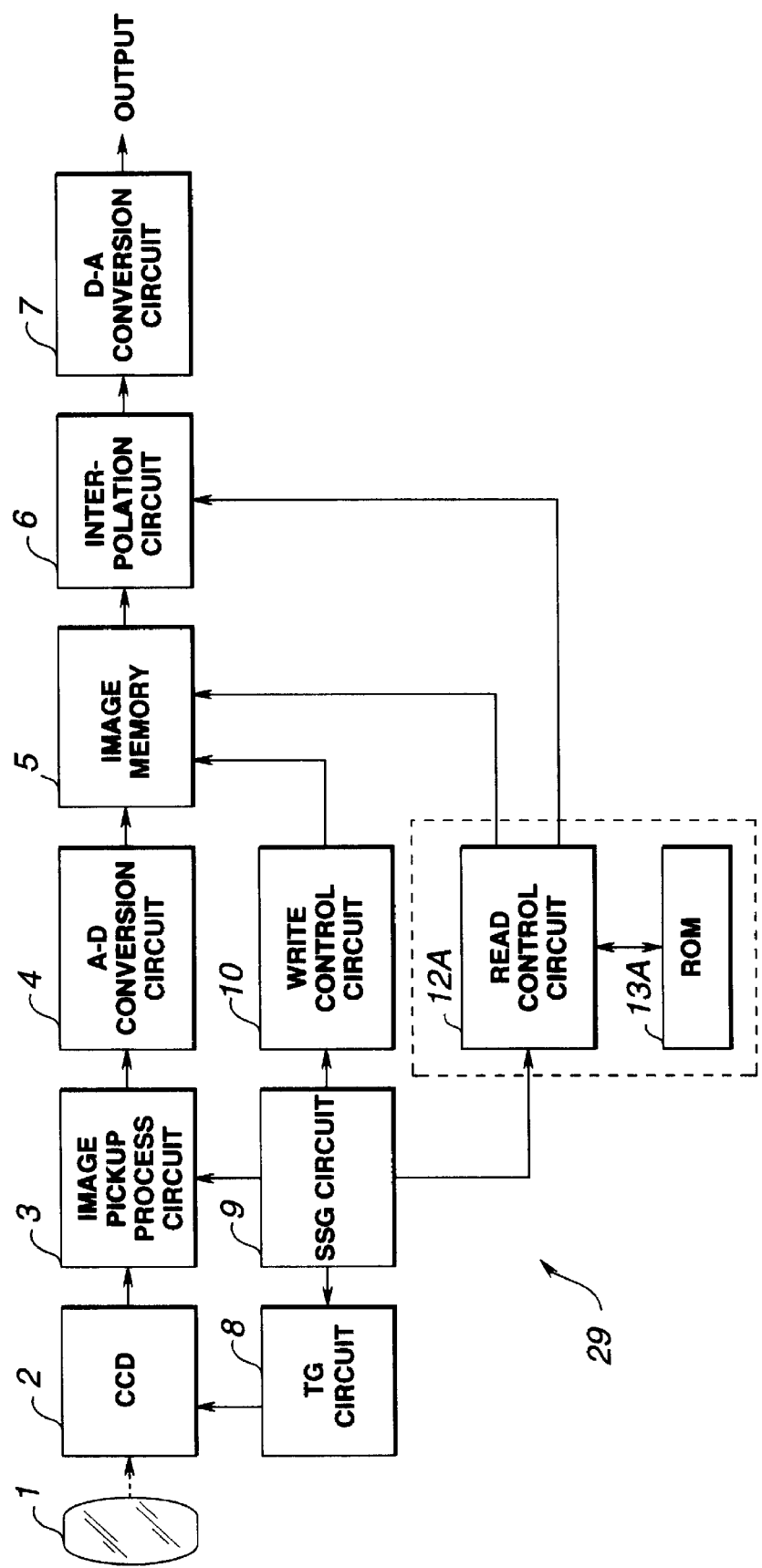
FIG. 3 is a block diagram showing the structure of an image processor of the prior art capable of correcting an optical distortion.
Figure 4:
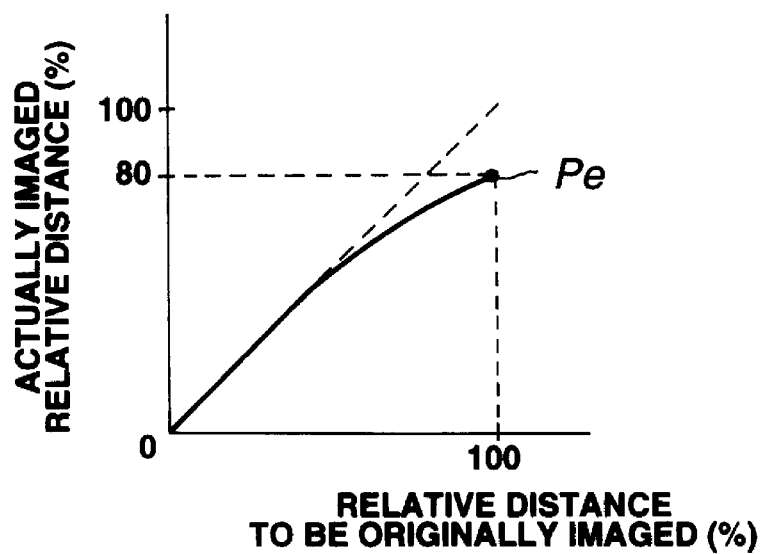
FIG. 4 is an illustration showing the optical distortion correction characteristic when an image with a barrel optical distortion is corrected by the image processor in FIG. 3.

The image processor 30B of this embodiment is different from the image processor 29 of the prior art in the correcting operation. In FIG. 8, each component which is the same as that in FIG. 3 is provided with the same symbol as that in FIG. 3 and its description is omitted.

Figure 5:
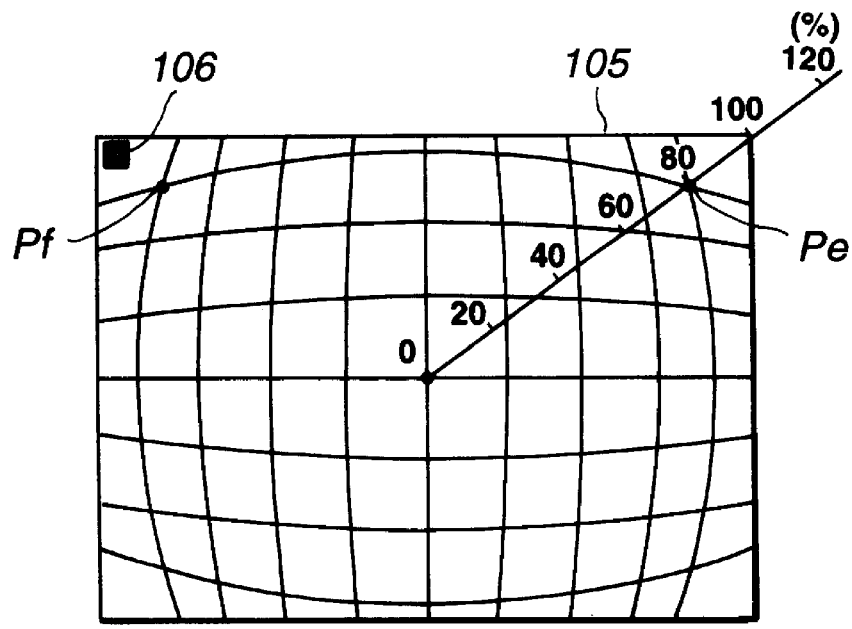
FIG. 5 is an illustration showing an image with a barrel distortion captured by a CCD.
Figure 9A:
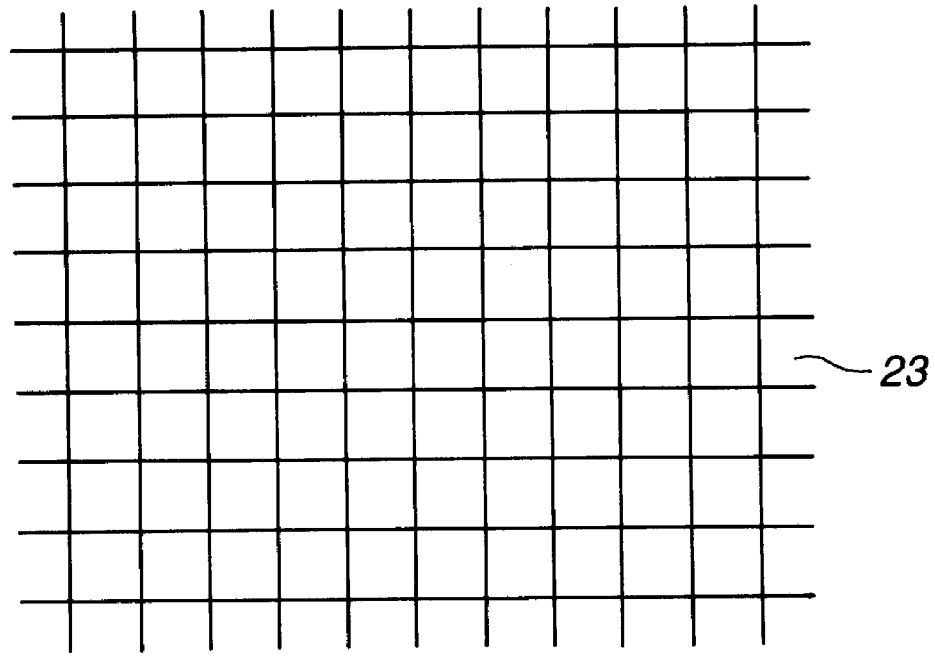
FIGS. 9A and 9B are illustrations showing a square-grid object and an image of the object corrected by the image processor in FIG. 8 respectively.

FIG. 9A shows a square-grid object 23. The object 23 is imaged by an optical system 1 on the image pickup surface 2A of the CCD 2 as a distortion-uncorrected image 105 shown in FIG. 5. Then, the image 105 is corrected by the image processor 30B so that it appears as a corrected image Gc in an output image area G0 corresponding to the image pickup surface 2A as shown in FIG. 9B.

Figure 9B:
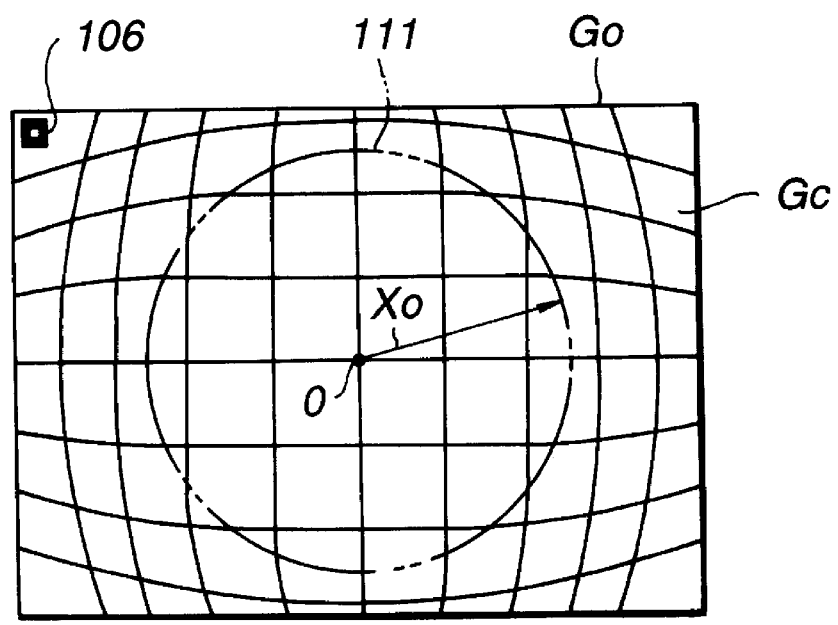

The image correction by the image processor 30B for generating the corrected image Gc shown in FIG. 9B uses two types of correction methods for an image on the image pickup surface 2A. The first correction method corresponds to the size of an effective image area (specifically, the image pickup surface 2A of the CCD 2) handled by the processor 30B, uses a circle 111 in which a relative distance (%) from the center O corresponding to an optical axis equals a predetermined radius X0 (%) on the image area G0 (specifically, the screen 27A of the monitor 27) which corresponds to an output and in which corrected output image data should be displayed as a correction boundary, and performs the first correction for electrically correcting an optical distortion of the optical lens 1 for a central closed area which is located at the optical axis side of the boundary. This correction is mainly performed by a change of read addresses by the $ROM_{13}$ a21a.

For a second closed area at the marginal side outside of the boundary circle 111, the second correction method is used which corrects the corrected picture element position of image data captured on the image pickup surface (or image pickup area) 2A of the CCD 2 (see FIG. 12) so that the position moves to the outside of the image area G0. This correction is mainly performed by change of read addresses by the ROM_b21b.

The relative distance from the optical axis center 0 is shown in terms of the percentage of the relative distance from the optical center when assuming the length ½ the diagonal line of the image pickup surface 2A (because the image pickup surface 2A is equivalently used together with an image storage area of the image memory 5 as described below, an image area G0' is used which is a high-order concept of the both meanings) as 100%.

In this embodiment, an image picked up by the CCD 2 is A-D-converted and thereafter stored in the image memory 5 temporarily and an optical distortion of the image data stored in the image memory 5 is corrected by means of address conversion or the like. Therefore, in fact, image data corresponding to the image picked up by the CCD 2 and stored in the image storage area of the image memory 5 is corrected.

Therefore, the pickup surface 2A of the CCD 2 and the image storage area of the image memory 5 are used as an equivalent meaning.

The above first and second correction methods are described below in detail. In the description of the methods, however, correction along the diagonal line of the image area G0' to be corrected is assumed as correction similarly performed for the whole of the image area G0' in fact.

Figure 10A:
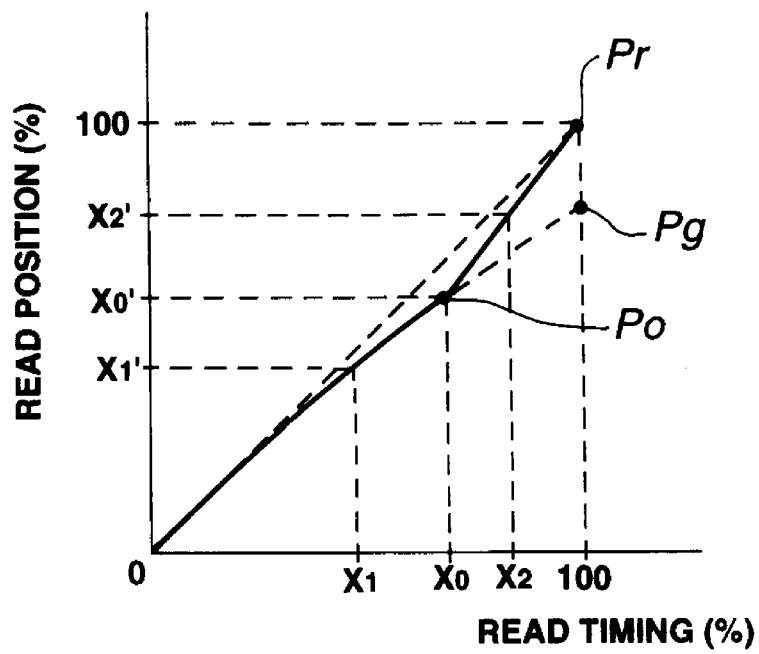
FIG. 10A is a correction characteristic diagram along the diagonal line of an image area of the image processor in FIG. 8.

FIG. 10A is a correction characteristic along the diagonal line of the image area G0 in the image processor of this embodiment, which shows the relation between the read position of the image memory 5 showing a relative distance on the corrected image area G0, that is, the read timing {display in terms of relative distance (%)} and the read position {display in terms of relative distance (%)} of image data in the uncorrected image area G0' corresponding to the read position.

Figure 6:
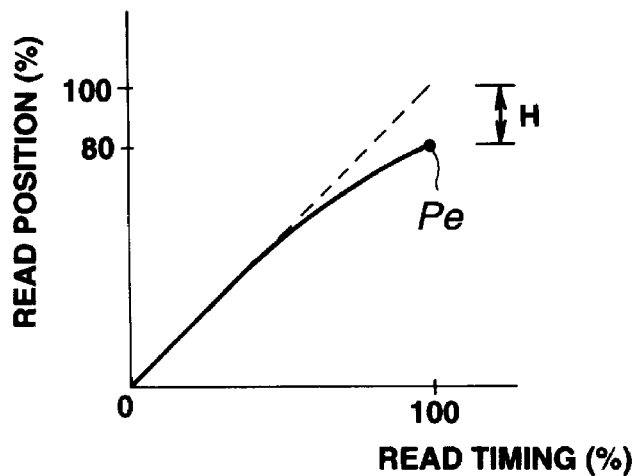
FIG. 6 is a characteristic diagram showing the relation between read timing and data read position for correction by the image processor in FIG. 3.
Figure 7:
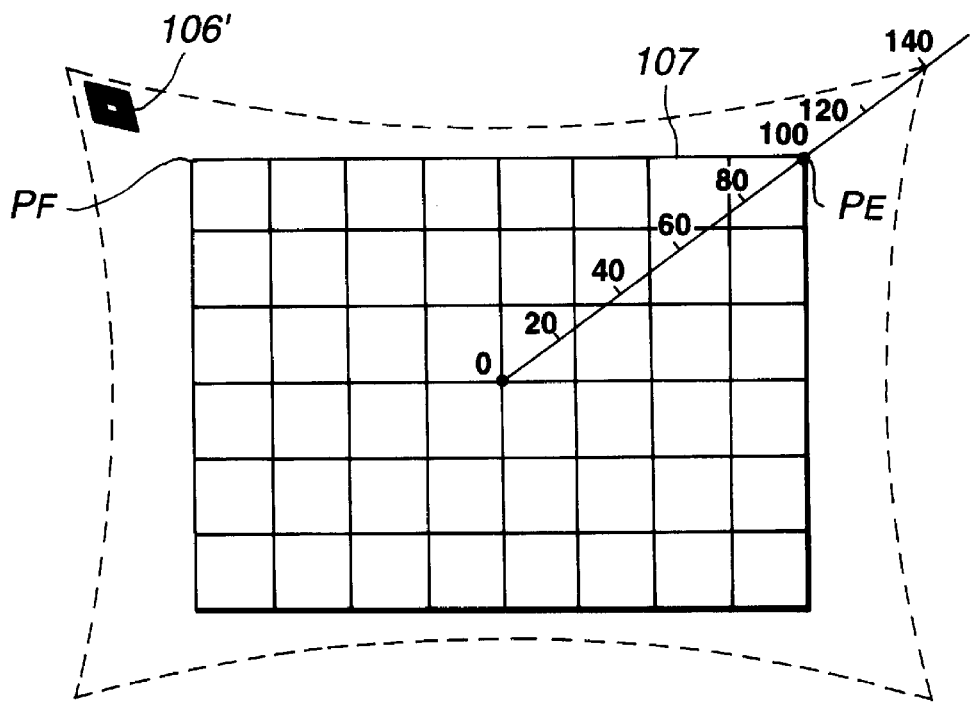
FIG. 7 is an illustration showing an image corrected by the image processor in FIG. 3.

The characteristic passing through the points P0 and Pg from the origin (optical axis center O) shows the barrel-optical-distortion correction characteristic in FIG. 6. Moreover, the linear characteristic from the origin (optical axis center O) to the point Pr is a characteristic when no correction is made. The image processor 30B performs correction along the characteristic line passing through the point P0 from the origin O and moreover through the point Pr from the point P0.

Figure 10B:
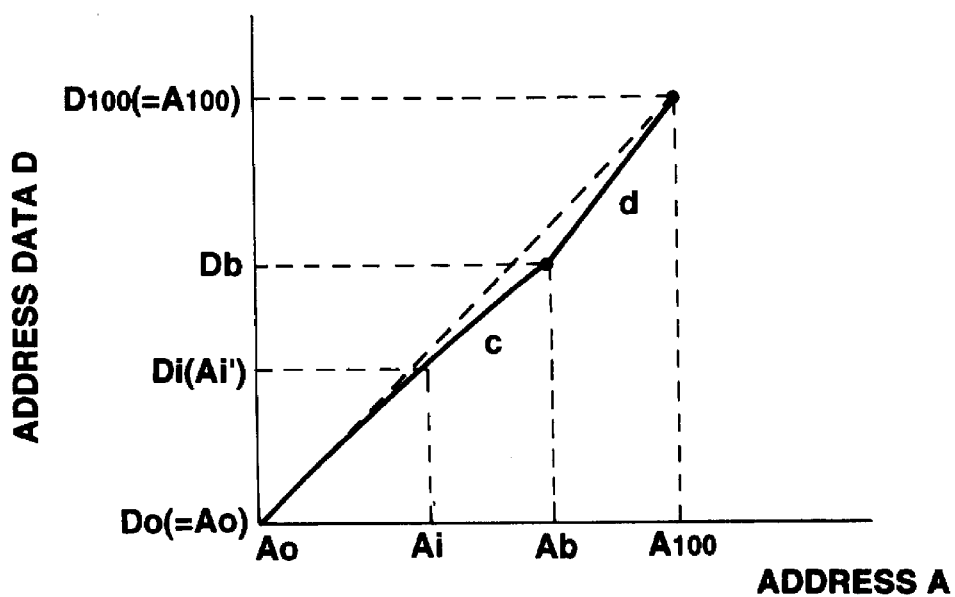
FIG. 10B shows the relation between read address and address data of a ROM.

The way of setting vertical and horizontal axes in FIG. 10A is the same as that in FIG. 6. Contents of FIG. 10A are almost equivalent to those of FIG. 10B. FIG. 10B schematically shows the relation between read address of the ROM 13B and address data D read by the read address (though address A actually comprises a horizontal-directional address and a vertical-directional address, it is shown by the percentage of the absolute value of the address along the diagonal line of FIG. 12).

As shown in FIG. 10B, address data Di is stored in a memory cell specified by each address Ai (i=0–100) of the ROM 13B. The address data Di shows a corrected address value Ai', and the address Ai and the address value Ai' have the relation shown by the continuous line.

Address conversion for correcting an optical distortion is performed in a central-side area corresponding to characteristic "c" and address conversion for preventing protrusion is performed in a marginal area of characteristic "d" outside of the boundary of the characteristic "c". For example, address data D0 for an address A0 coincides with the address A0 and address data D100 for an address A100 coincides with the address A100. Moreover, an address Ab shows the address of the boundary. In this case, address data Db is read. Thus, address data D read out of the ROM 13B is applied to an address end of the image memory 5 as a corrected address and a picture element of a memory cell corresponding to the address is read.

As shown by the characteristic in FIG. 10B, because the characteristics "c" and "d" are connected by the boundary, a corrected image obtained through the address conversion is a continuous image in which discontinuation such as missing of a picture element at a boundary does not occur.

Figure 11:
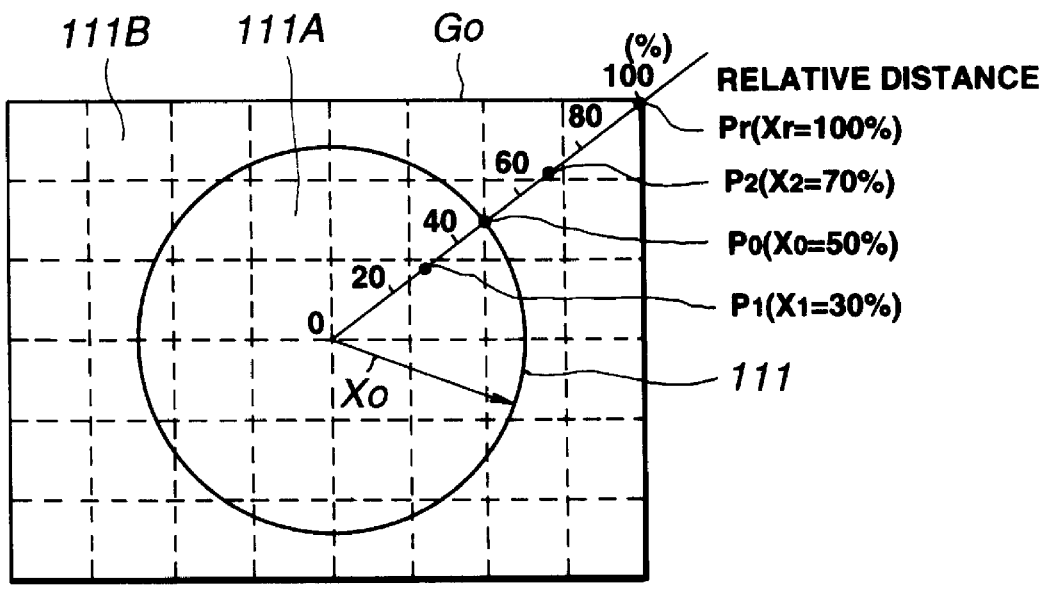
Figure 12:
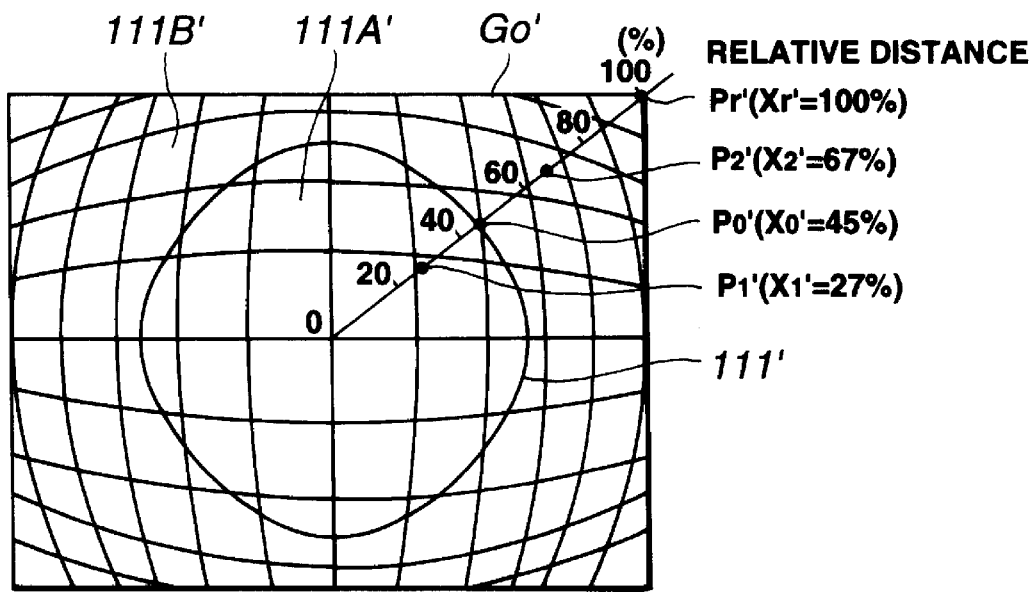

FIG. 11 shows an undistorted image formed on the image area G0 on which the circle 111 providing a correction boundary and the undistorted square-grid line (broken line) are shown. FIG. 12 is an illustration in which an optical distortion line corresponding to the undistorted grid line (broken lin) in FIG. 11 is entered in the uncorrected image area G0' captured by the CCD 2 or image memory 5. It is a matter of course that the outline of the image area G0 in FIG. 11 fits that of the image area G0' in FIG. 12.

The image processor 30B applies the first correction which is optical distortion correction corresponding to the characteristic line from the origin O to the point P0 to the central portion of an image inside of the circle 111 providing a correction boundary within a range of the relative distance of the radius X0 on the image area G0. Moreover, the processor 30B applies the second correction which is correction corresponding to the characteristic line of the straight line connecting the point P0 with the point Pr to the marginal portion outside of the circle 111 whose relative distance on the image area G0 ranges between the outside of the radius X0 and the relative position (100%) at an end of the image area.

That is, in an area in the circle 111 on the image area G0, the processor 30B captures image data at the read position of an image in the uncorrected image area G0' according to the characteristic line of the point P0 from the origin 0 to the read position at the timing of each read position as image data on the image area G0 and corrects the image data in accordance with the above optical distortion correction.

Specifically, at the timing of a read position X1 (e.g. 30%) which is an optional position on the image area G0, image data of a corresponding read position X1' (e.g. 27%) on the image area G0' of an uncorrected image is read in the case of this lens and output as corrected data. Moreover, on the circle 111 serving as a correction boundary, image data of a corresponding read position X0' (e.g. 45%) on the image area G0' of the uncorrected image is read at the timing of a read position X0 (e.g. 50%).

In an area outside of the circle 111 on the image area G0, the processor 30B captures image data at a read position to which a read position with a predetermined interval on the image area G0 corresponds on the uncorrected image area G0' at the timing of the read position with the predetermined interval as image data at a read position on the image area G0 in accordance with the characteristic line connecting the point P0 with the point Pr. The processor 30B performs the above processing from the circle 111 providing a boundary on the image area G0 up to the end Pr.

Specifically, for a read position X2 (e.g. 70%) which is an optional position outside of the circle 111 on the image area G0, image data at a corresponding read position X2' (e.g. 67%) on the uncorrected image area G0' is read from a correction characteristic line and output as corrected data. While a read position Xr is 100% on the end Pr of the image area G0, a corresponding read position Xr' on the uncorrected image area G0' also comes to 100% and image data of an uncorrected end is directly read and output as image data of a corrected end.

As described above, at the timing for reading the relative distance 100% at the end Pr of the image area, an uncorrected image stored in the relative distance 100% of the uncorrected image area G0' is read and one point always corresponds to one point for horizontal and vertical axes. Therefore, the information of an image in the uncorrected image area G0' does not protrude to the outside of the image area G0 serving as a corrected output image area.

The specific values used for the read positions X0', X1', and X2' are values shown for reference and they are changed due to the optical distortion characteristic of the optical lens 1 or the like. Moreover, the size of the circle 111 is not restricted to the above value. It is possible to set the size to a value suitable for the processor 30B. Furthermore, it is possible to use not only a circle but also an ellipse or quadrangle as an area providing a correction boundary.

FIG. 9B shows an image area corrected by the above correction method, in which the optical distortion of the central portion of the image area G0 is corrected and the object image is returned onto an undistorted grid. Moreover, because the marginal portion of the image is corrected so that it does not protrude to the outside of the image area G0, the top left image "□" 106 in FIG. 5 remains in the image area G0 in FIG. 9B. The circle 111 shown by a two-dot chain line in FIG. 9B serves as a correction boundary for providing a change point of correction characteristics from the first correction to the second correction.

As described above, in the case of the correction ROM 13B serving as information storage means shown in FIG. 8, a corrected address predetermined for an address showing the read position of the image area G0 is stored in the ROM_a21a and ROM_b21b about each portion of an image area.

For example, as shown in FIG. 11, an address value for the first correction showing a relational position for correcting an optical distortion value determined by the relation between the grid line on the image area G0 in FIG. 11 and the distorted grid line on the image area G0' in FIG. 12 is stored in the ROM_a21a as a corrected address value at the central portion 111A (however, the central portion 111A' is used in the case of the uncorrected image area G0 ) in the circle 111 providing the correction boundary of the image area G0.

Moreover, at the marginal portion 111B of the image outside of the circle 111 providing a correction boundary, an address value for the second correction for capturing all uncorrected image data of the marginal portion 111B' from the boundary line 111' up to the image area end on the uncorrected image area G0' corresponding to the circle 111 by making the data correspond to the marginal portion of the image area G0 is stored in the ROM_b21b as a corrected address value so that the image does not protrude to the outside of the image area G0.

For example, address values which corresponds to the address values providing the relative distances (%) X0, X1, X2, and Xr shown in Figs. 10A, 11, and 12 and provides relative distances (%) X0', X1', X2', and Xr' serve as the above corrected address values.

Then, the uncorrected image data captured by the CCD 2 is stored in the image memory 5 serving as image storage means correspondingly to each address. The read control circuit 12A serving as read control means refers to the data stored in the correction ROM 13B, reads image data stored in corrected read addresses corresponding to read positions from the image memory 5 in accordance with a read signal, corrects an optical distortion, and outputs an image signal on the image area G0 to an interpolation circuit 6 so that image information does not protrude to the outside of the image area. A corrected signal is provided with the interpolation between picture elements (e.g. weighting correction) by the interpolation circuit 6, thereafter converted into an analog signal by the D-A conversion circuit 7 and moreover converted into a standard picture signal by the encoder 28, and output to the monitor 27 or the like.

The above described image processor 30B of this embodiment electrically corrects distortions of the central portion of an image due to an optical system for captured image information and thereby, the image becomes an undistorted normal image or a slightly distorted image. Moreover, because the marginal portion from which information must not be lost is electrically corrected so that the portion does not go out of a display area or display image area without correcting optical distortions, it is possible to prevent a trouble that an image portion formed on the marginal portion of the image pickup surface is lost by correcting optical distortions like the case of the processor 29 of the prior art. Furthermore, because the image pickup surface or the circle with a predetermined radius on a screen (to be set correspondingly to an image pickup screen) is used as a boundary for the above correction, even an image whose correction characteristics are changed can be displayed as a more natural image and observed.

Therefore, when a wide-angle optical system is used for an image pickup apparatus, an image can be displayed without losing the marginal image portion. Moreover, this embodiment makes it possible to basically correct an optical distortion of the central portion only by changing read addresses and obtain a high-quality image, and moreover perform correction for preventing the marginal portion from protruding by changing addresses with a characteristic different from that of the central portion. Therefore, it is possible to realize the image processor 30B with a simple or small circuit and decrease the cost of the processor 30B.

Then, an endoscope system is described below which is provided with a modification of the first embodiment to which an endoscope is applied. In the case of this modification, it is one of the objects to provide an image processor capable of electrically correcting an image without increasing the outside diameter of the inserting portion of the endoscope.

Figure 13:
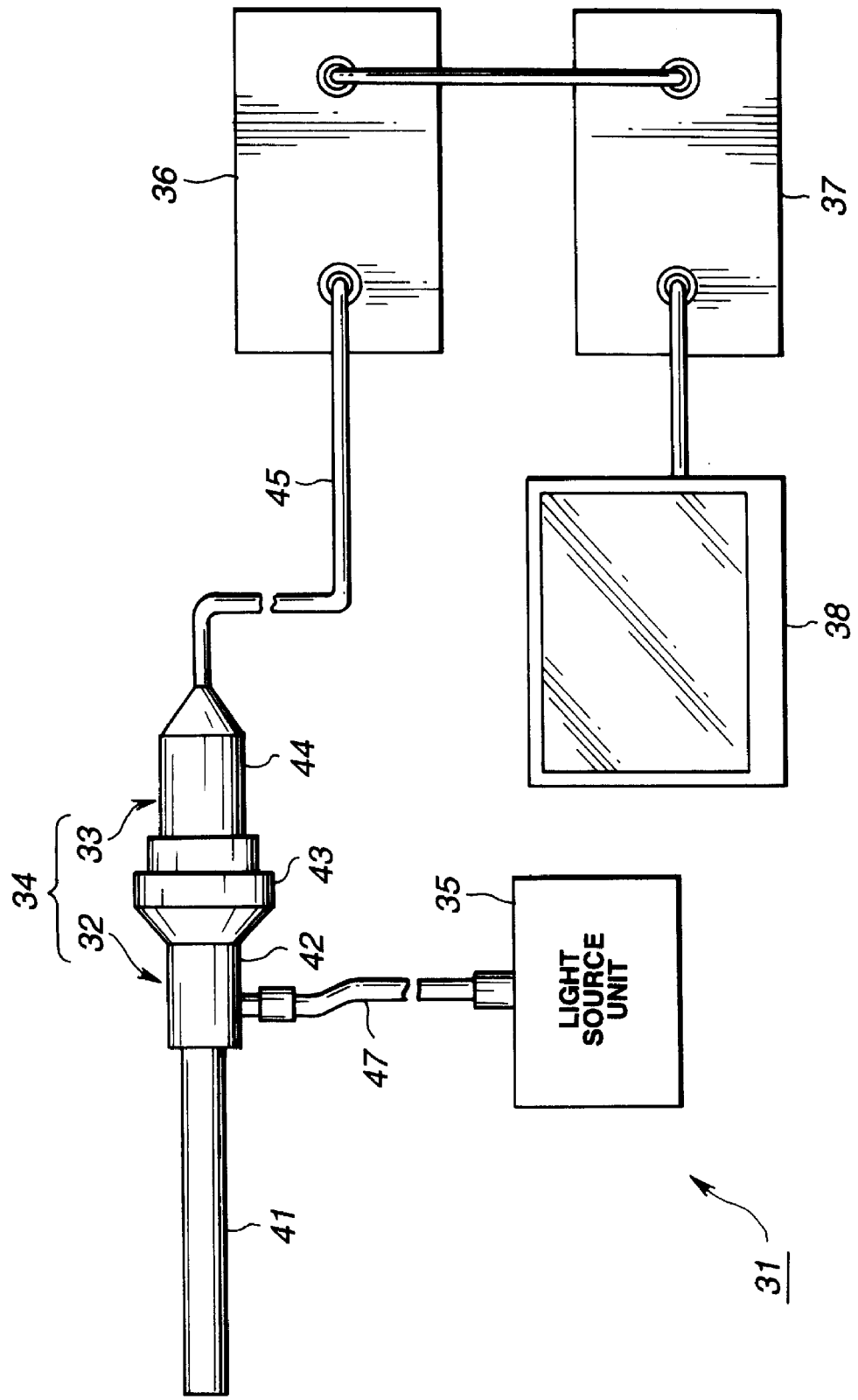
Figure 14:
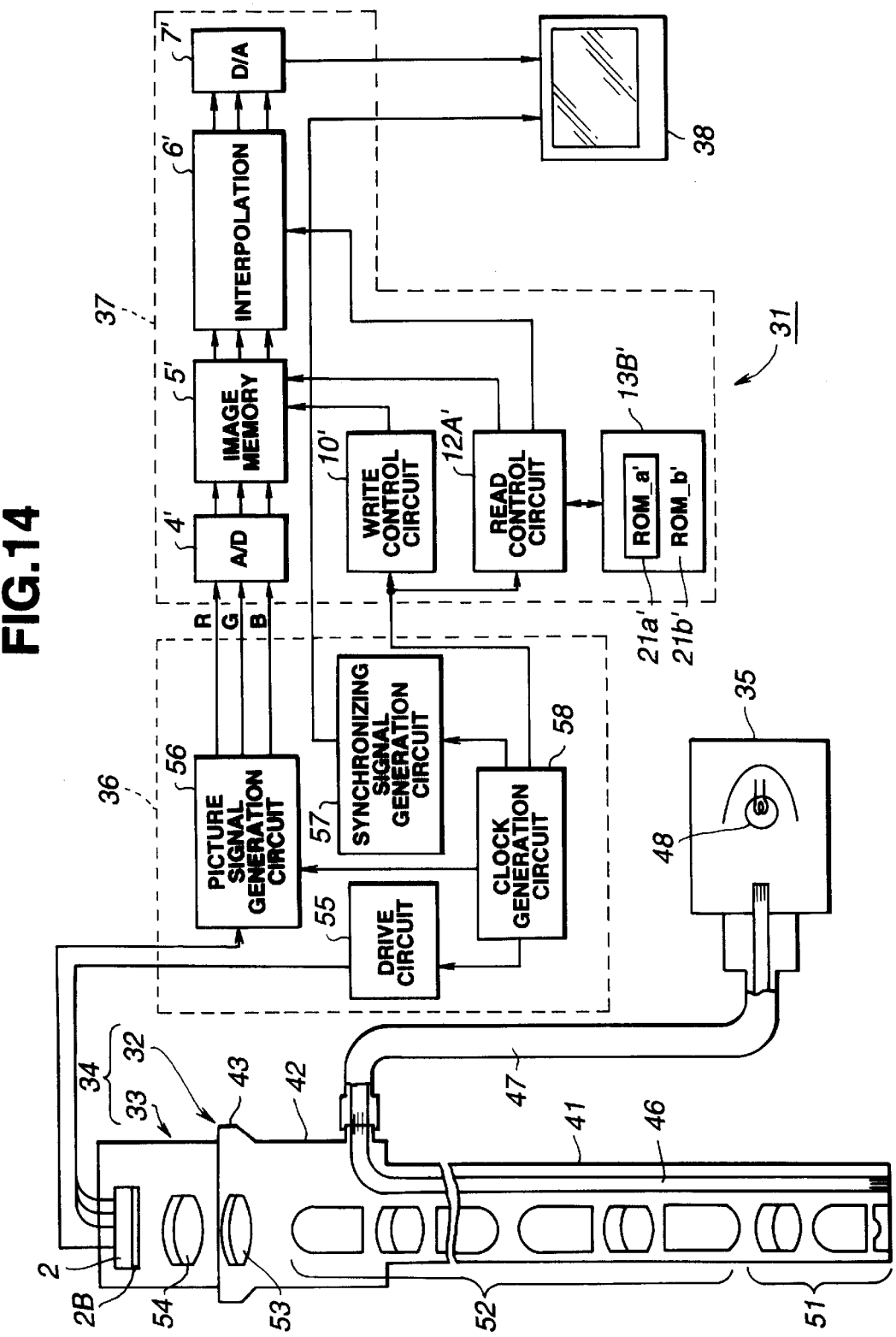

FIG. 13 shows the overall structure of an endoscope system and FIG. 14 shows the internal structure of the system. In FIGS. 13 and 14, an endoscope system 31 comprises a TV-camera-mounted endoscope 34 in which a TV camera 33 is mounted on a rigid endoscope 32, a light source unit 35 for supplying illumination light t o the rigid endoscope 32, a camera control unit (hereafter referred to as a CCU) 36 for performing signal processing for an image pickup device built in the TV camera 33, an image processing unit 37 for preventing the marginal portion of an image from protruding and correcting distortion of the central portion of the image, and a color monitor 38 for displaying a picture signal in which the distortion of the central portion of the image is corrected and the marginal portion of the image is prevented from protruding. It is also possible to record a picture signal passing through the image processing unit 37 in a picture-signal or image recorder.

The rigid endoscope 32 has a rigid slender inserting portion. A thick gripping portion 42 to be held by an operating surgeon is formed at the rear end of the inserting portion 41 and an eye contacting portion 43 is formed at the rear end of the gripping portion 42. It is possible for an operating surgeon to perform observation through an eye contacting window of the eye contacting portion 43 and also possible to set a TV camera heat 44 of the TV camera 33 to the eye contacting portion 43. A cable extended from the TV camera head 44 is connected to the CCU 36.

As shown in FIG. 14, a light guide 46 is inserted into the inserting portion 41 of the rigid endoscope 32 and the light guide 46 is connected to the light source unit 35 from the light guide mouthpiece of the gripping portion 42 through a light guide cable 47. Moreover, white light generated by a lamp 48 in the light source unit 35 is supplied to the light guide 46 through the light guide cable 47 and the white light transmitted by the light guide 46 is emitted to a forward object such as an affected part from the front end (of the light guide 46) as illumination light.

The illuminated object is optically imaged by an objective system 51 set at the front end of the inserting portion 41 and the image of the object is transmitted toward the rear side by passing through a relay lens system 52. The final image transmitted to the vicinity of the rear end of the gripping portion 42 can be enlarged and observed by an eyepiece system 53. When the TV camera 33 having a built-in image pickup device is mounted, the final image is formed on the CCD 2 by further passing through an imaging lens system 54.

A mosaic filter 2B for optically separating colors is set to the image pickup surface (photoelectric transfer surface) of the CCD 2 to separate colors every picture element. An image pickup signal photoelectrically-transferred by applying of a CCD drive signal generated by a drive circuit 55 is output to the CCD 2 as an output signal and the output signal is input to a picture signal generation circuit 56.

Color signals of, for example, R, G, and B are generated by the picture signal generation circuit 56 and output to the image processing unit 37 as standard picture signals together with a synchronizing signal output from a synchronizing-signal generation circuit 57. The CCU 36 has a built-in clock generation circuit 58 for generating a reference clock and the reference clock is input to the drive circuit 55 for generating a CCD drive signal, the picture signal generation circuit 56 for generating a picture signal, and the synchronizing signal generation circuit 57 for generating horizontal and vertical synchronizing signals, and each signal is generated synchronously with the clock.

The color signals of R, G, and B output from the picture signal generation circuit 56 are converted into digital color signals by an A-D conversion circuit 4' comprising three A-D converters and the digital color signals are temporarily written in an image memory 5' comprising a frame memory or field memory in accordance with a write control signal sent from a write control circuit 10'.

The image data stored in the image memory 5' is read in accordance with a read control signal sent from a read control circuit 12A' by referring to the corrected information previously written in a correction ROM 13B' and moreover interpolated by an interpolation circuit 6'. The write control circuit 10' and the read control circuit 12A' constitute read/write control means for controlling read/write operation for the image memory 5' serving as image storage means.

The image data interpolated by the interpolation circuit 6' is converted into an analog color signal by a D-A conversion circuit 7' and output to the color monitor 38 as a picture signal together with a synchronizing signal.

The structure shown in FIG. 14 supplies clocks generated by the CCU 36 to the write control circuit 10' and read control circuit 12A' in the image processing unit 37 and generates write and read control signals.

The contents of the distortion correction in the image processing unit 37 are basically the same as those of the distortion correction of the first embodiment.

Therefore, the ROM 13B' comprises a ROM_a'21a' for performing the correction to remove an optical distortion by changing read address values for the central portion of an image and a ROM_b'21b' for performing the correction to prevent the marginal portion of the image from going out of a display screen.

Figure 15:
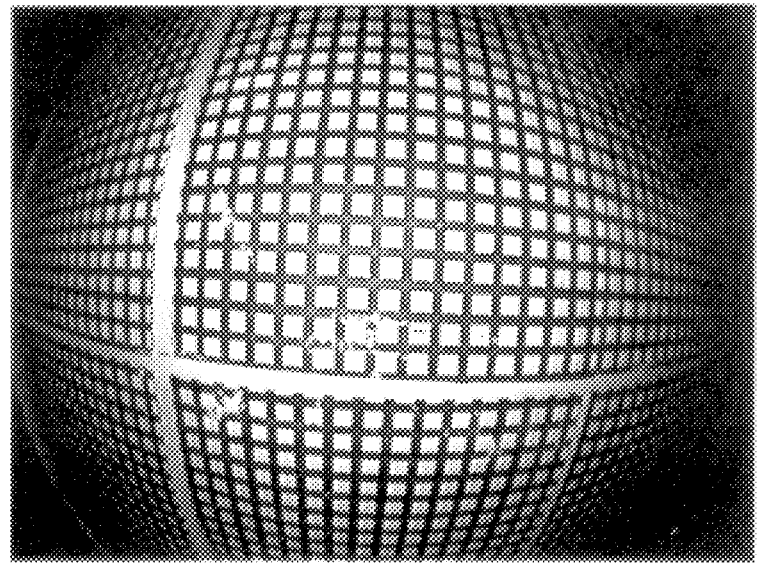
Figure 15:
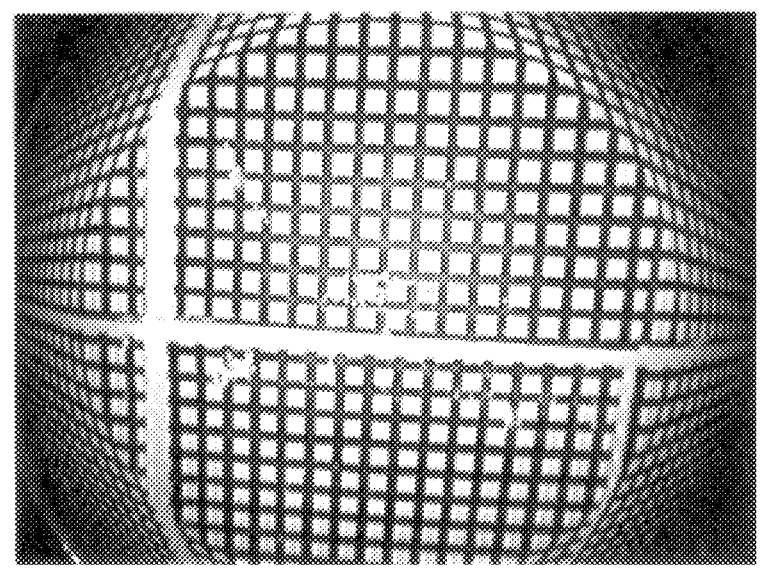

When assuming that FIG. 15A shows an image (equivalent to an image whose distortion is not corrected by an optical system) obtained by displaying a picture signal output from the CCU 36 when picking up, for example, a square-grid-like object, FIG. 15B shows an image when displaying a picture signal provided with the correction for distortion of the central portion and the correction for prevention of protrusion of the marginal portion on the color monitor 38. Thus, the image in FIG. 15B is displayed under the state in which the central portion is corrected like a square grid and the marginal portion is prevented from protruding.

Therefore, when performing endoscope inspection by using the endoscope system 31, the distortion of the central portion is corrected and observation can be made at a high resolution on the display screen of the color monitor 38. Moreover, because a wide range is displayed though the marginal portion has a distortion, it is possible to roughly confirm the state of a forceps to be inserted from or extracted to the outside and easily perform therapy or surgical removal.

Moreover, when applying optical-distortion correction not to the whole image but to only the central portion, simple correction is enough in many cases compared to the case in which wide-range correction is necessary like the marginal portion, the correction time can be decreased, and conditions requested to a device for performing correction are moderated (for example, the condition for high-speed operation of the device is moderated and the cost can be decreased).

Moreover, when it is requested that an optical system to be used is small and has a wide angle like an endoscope for which it is requested that the outside diameter of an inserting portion to be inserted into a patient or the like is as small as possible, a distortion is easily further intensified. However, this modification makes it possible to electrically correct the distortion. Therefore, a pain of a patient can be moderated because it is unnecessary to increase the diameter of the inserting portion.

Moreover, an operating surgeon can easily perform endoscope inspection or take actions because the distortion of the central portion of an image for which a high resolution is desired is removed and the marginal portion of the image can also be observed.

Lenses shown by symbols 51 to 54 in FIG. 14 correspond to the optical lens 1 in FIG. 8. The ROM 13B' stores corrected address data for performing the correction to mainly remove distortion from the central portion of a distorted image formed on the image pickup surface of the CCD 2 and corrected address data for performing the correction to prevent the marginal portion from protruding.

In the case of the structure in FIG. 14, the image processing unit 37 uses a clock generated by the CCU 36 without using a circuit for generating a clock. Instead of the structure, however, it is also possible to generate write and read control signals by setting a clock generation circuit for capturing a synchronizing signal output from the CCU 36 and generating a clock synchronizing with the synchronizing signal in the image processing unit 37.

By using the above structure, it is possible to generate a picture signal corresponding to a distorted image whose marginal portion can be prevented from protruding and whose central-potion distortion can be corrected obtained from an existing endoscope system by setting the image processing unit 37 of this modification between the CCU and the color monitor of the existing endoscope system.

Therefore, it is possible to provide an image processor to be widely used. Moreover, it is possible to decrease the economic burden of a user because an image whose marginal portion can be prevented from protruding and whose central-portion distortion can be corrected can be obtained only by adding the image processing unit 37 to an existing endoscope system.

Moreover, it is described in FIG. 14 that a color signal is generated as a picture signal by the picture signal generation circuit 56. However, without being restricted to this structure, it is also possible to use a structure for generating a luminance signal (Y) and two color difference signals (R-Y and B-Y).

Furthermore, it is possible to constitute the CCU 36 in FIG. 14 by using the TG circuit 8, image pickup process circuit 3, and SSG circuit 9 shown in FIG. 8 instead of the drive circuit 55, picture signal generation circuit 56, clock generation circuit 58, and synchronizing signal generation circuit 57 which constitute the CCU 36.

Furthermore, it is possible to use the image processing unit 37 shown in FIG. 14 for a picture signal output from a picture signal recorder recording picture signals. For example, it is also possible to display a picture signal corresponding to an endoscope image recorded in a VTR or the like used as a peripheral unit of an endoscope system on a display through the image processing unit 37.

The image processor of the second embodiment of the present invention is described below.

Though the image processor 30B of the first embodiment uses a structure for storing a corresponding address in the correction ROM 13B so that the whole image area can be corrected, the capacity of the correction ROM 13B must be increased to store corrected addresses of the whole image area. Therefore, it is an object of the second embodiment to decrease the scale of a circuit and further decrease the cost.

Therefore, the image processor of this embodiment is characterized by assuming that characteristics of an optical distortion in four quadrants are line-symmetric to horizontal and vertical axes, storing corrected addresses for one quadrant in a ROM, obtaining the characteristics of remaining three quadrants by a simple operation, and thereby minimizing the capacity of a correction ROM.

Figure 16:
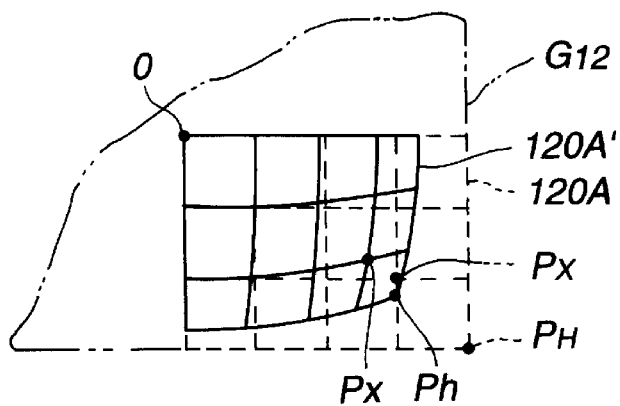
FIG. 16 is an illustration showing a screen related to the fourth quadrant among all screens applied to an image processor of second embodiment of the present invention and an image to be corrected.

FIG. 16 shows an image area 120A of the fourth quadrant equivalent to ¼ an image area G12 and an uncorrected image area 120A' of the fourth quadrant of an image captured by a CCD corresponding to the image area 120A.

Figure 19:
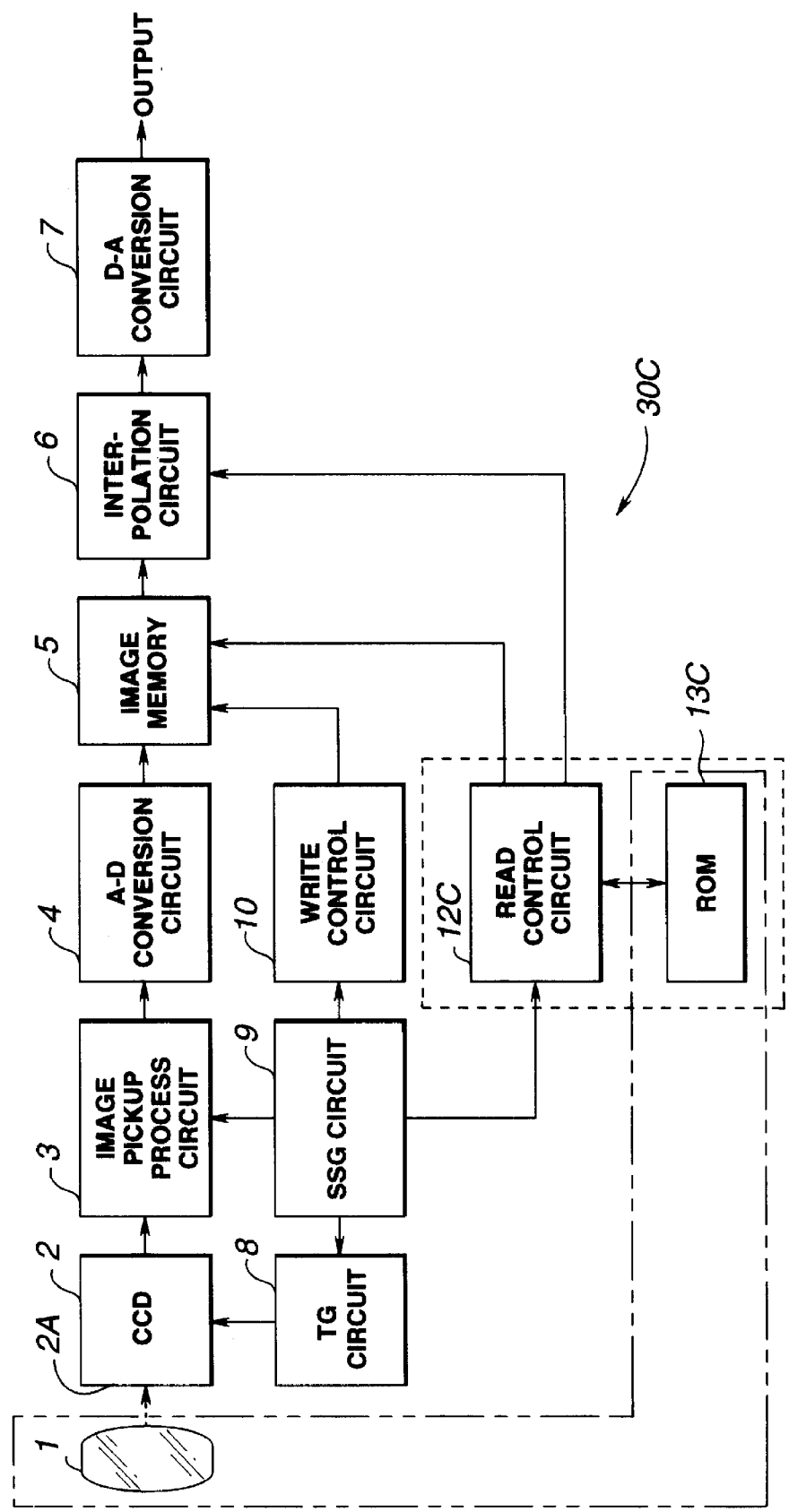
FIG. 19 is a block diagram showing the structure of the image processor of the second embodiment in FIG. 16.

In the case of the processor of this embodiment, each read position of the image area 120A of the fourth quadrant such as the read position of the uncorrected image area 120A' corresponding to a point PH or PX, that is, an address value showing a point Ph or Px and serving as address conversion information is stored in a correction ROM 13C serving as processing-information holding means (see the block diagram in FIG. 19).

A method for obtaining a corrected address value of other quadrant in accordance with a corrected address value of the fourth quadrant is described below by referring to the image area conversion diagrams in FIGS. 17A, 17B, and 17C.

Figures 17A, 17B, 17C:
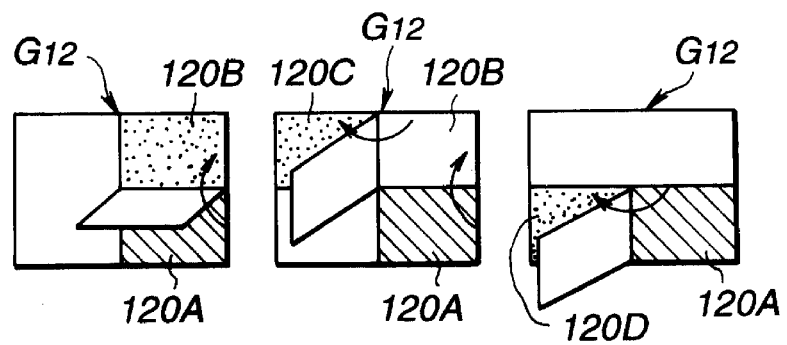
FIGS. 17A to 17C are illustrations showing conversion states for obtaining corrected address information related to the fourth quadrant in the image processor in FIG. 16 by converting the information into information for other quadrant.

As shown in FIG. 17A, an image area 120B of the first quadrant is obtained by rotating the image area 120A of the fourth quadrant about the horizontal axis. A corrected address value in the image area 120B of the first quadrant is obtained by applying rotational conversion similar to that of the image area 120A to corrected address value data of the fourth quadrant.

Moreover, as shown in FIG. 17B, the image area 120C of the second quadrant is obtained by rotating the image area 120B of the first quadrant about the vertical axis. A corrected address value in the image area 120C of the second quadrant is obtained by applying rotational conversion similar to that of the image area 120B to corrected address value data of the first quadrant.

Furthermore, as shown in FIG. 17C, the image area 120D of the third quadrant is obtained by rotating the image area 120A of the fourth quadrant about the vertical axis. A corrected address value in the image area 120D of the third quadrant is obtained by applying rotational conversion similar to that of the image area 120D to corrected address value data of the fourth corrected address value data.

Figure 18:
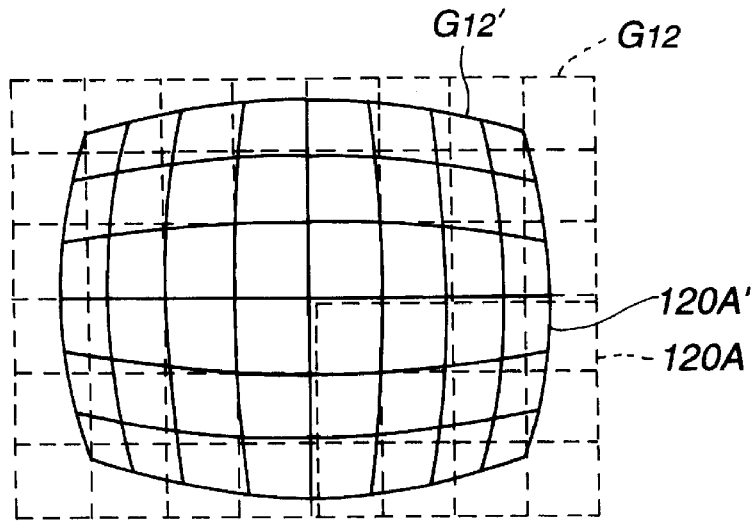
FIG. 18 is an illustration showing the distorted states of all screens in accordance with the corrected address information obtained through the conversion shown in FIGS. 17A to 17C.

As described above, the characteristic of the whole corrected address of an uncorrected image area G12' for the image area G12 corresponding to an output image as shown in FIG. 18 by performing various types of conversion in accordance with the corrected address data of the fourth quadrant equivalent to ¼ image area and obtaining corrected address data of other remaining quadrants as if folding a piece of paper.

The circuit structure and operation of the image processor 30C of this embodiment for performing the above corrected address conversion are described below by referring to the block diagrams in FIGS. 19 and 20.

Though the structure of the processor 30C of this embodiment shown in FIG. 19 is different from the structure in FIG. 8 in the read control circuit 12C serving as read control means and the correction ROM 13C serving as processing-information holding means, other components are the same as those in FIG. 19. Therefore, the same component is provided with the same symbol.

Moreover, in the case of the processor 30 of this embodiment, the lens 1 and ROM 13C are simultaneously detachable so that they can be replaced with others as shown by a two-dot chain line. That is, to use a lens 1 having an imaging characteristic different from the present lens 1, the present ROM 13C is replaced with a ROM 13C corresponding to the replaced lens 1 so that correction suitable for the lens 1 to be actually used can be made.

Furthermore, the image processor of this embodiment has a structure in which the read control circuit 12C reads data from the image memory 5 by the ROM 13C storing corrected addresses. The block diagram in FIG. 20 shows details of the portion including the read control circuit 12C and correction ROM 13C enclosed by a broken line.

Figure 20:
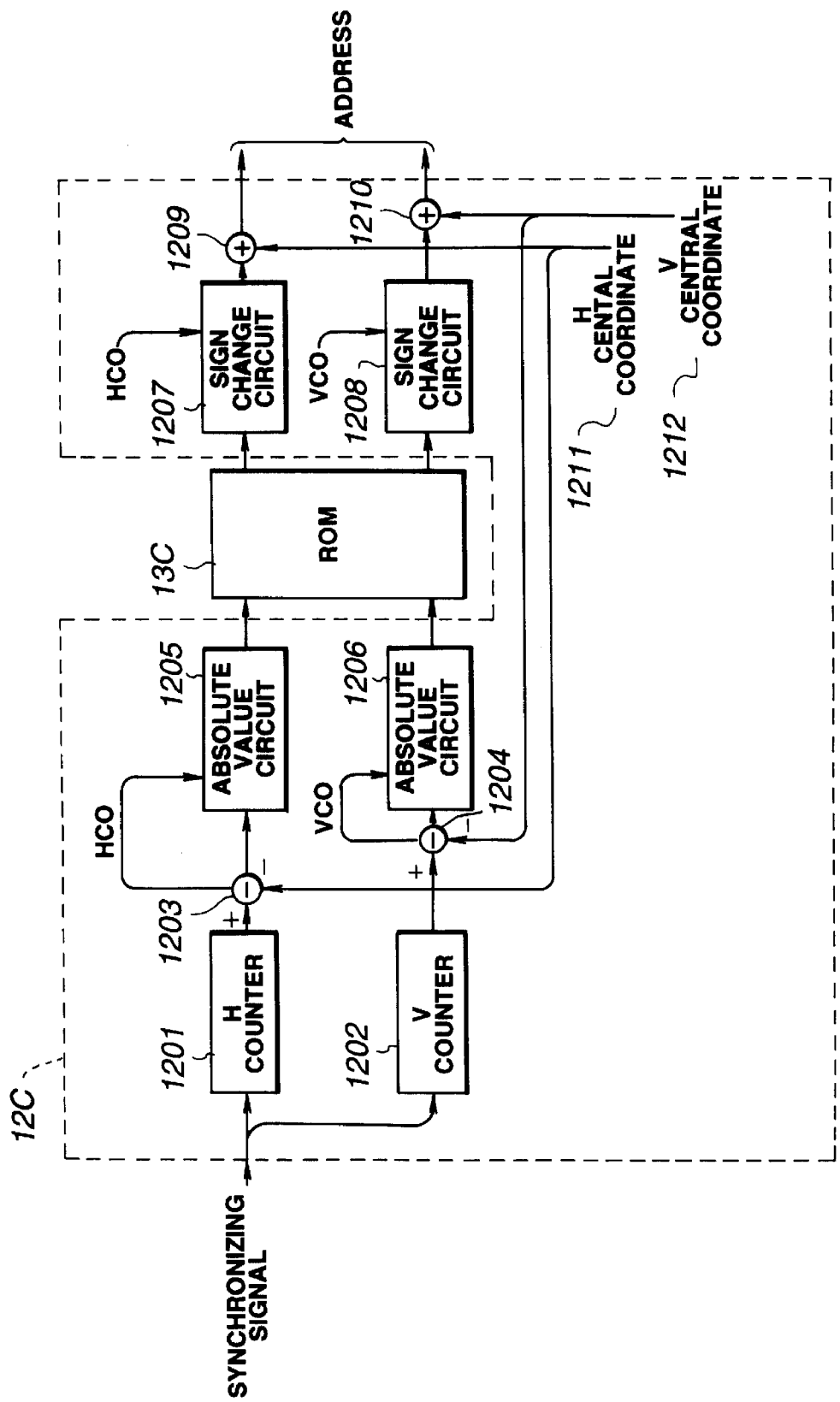
FIG. 20 is a block diagram showing detailed structures of a read control circuit and a correction ROM of the block diagram in FIG. 19.
Figure 21:
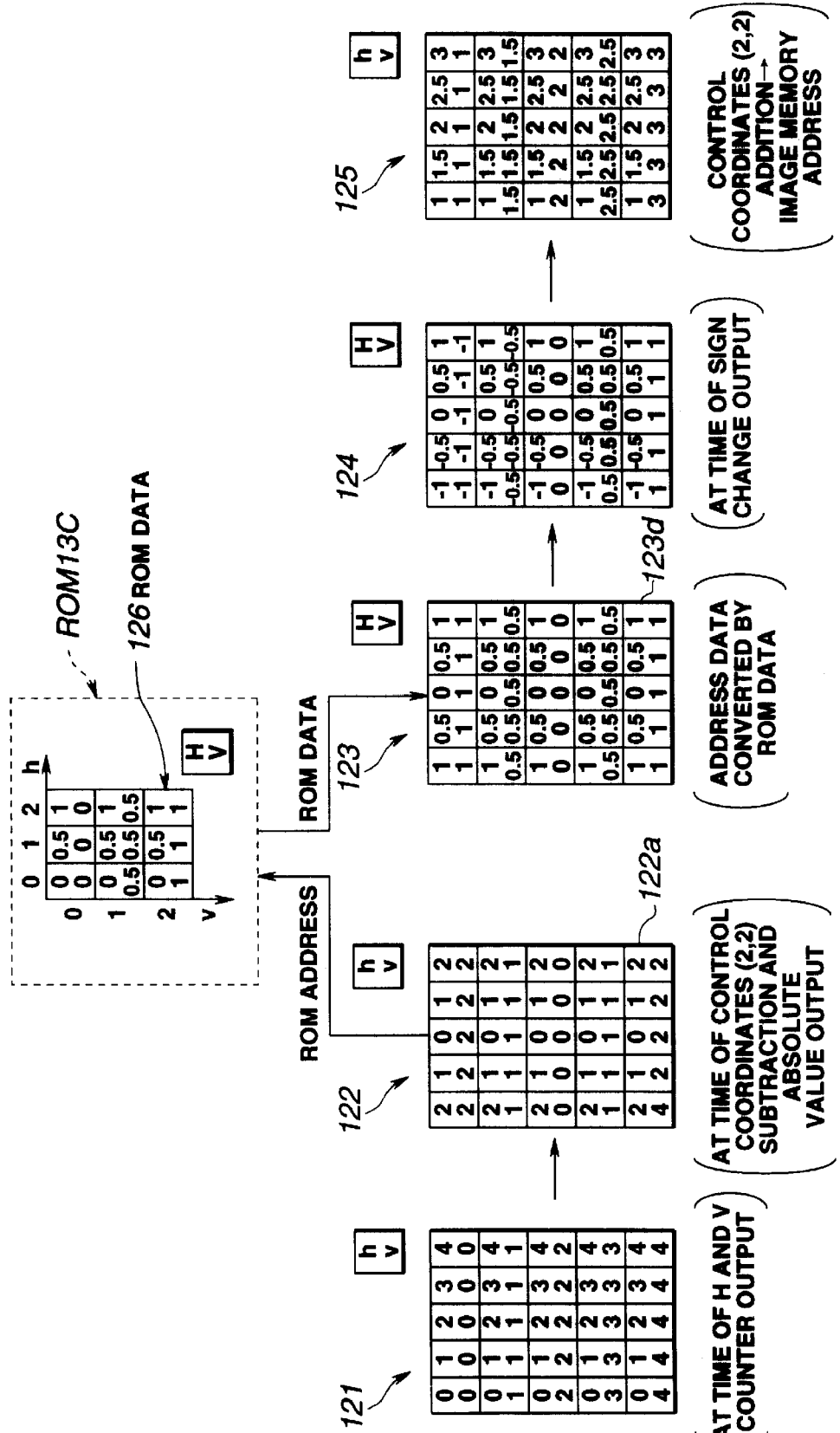
FIG. 21 is an illustration for explaining the conversion state of the read control circuit in FIG. 20 in accordance with picture-element coordinates.

In FIG. 20, the portion enclosed by a broken line corresponds to the read control circuit 12C. FIG. 21 explains a conversion state of the read control circuit 12C in FIG. 20 by using coordinates with a small number of picture elements. In FIG. 21, the whole image area comprises 5×5 picture elements and the central coordinates are shown as (2, 2). Moreover, in each picture-element block on each image area represent, an upper-stage value represents a horizontal-directional counted value h or horizontal corrected data H and a lower-stage value represents a vertical-directional counted value v or vertical corrected data V.

First, an image area is counted from the top left toward the bottom right like scanning lines of a TV in accordance with a synchronizing signal input to the read control 12C by an H counter 1201 for counting address values in the horizontal direction(H) of an image and a V counter 1202 for counting address values in the vertical direction (V).

The counted results are shown as counted values in the counted data 121 corresponding to the image area in FIG. 21.

Outputs of the counters 1201 and 1202 are input to subtracters 1203 and 1204 respectively. Central coordinate values 1211 and 1212 are input to other input terminals of the subtracters 1203 and 1204. Moreover, outputs of the subtracters 1203 and 1204 are input to absolute value circuits 1205 and 1206.

Outputs of the absolute value circuits 1205 and 1206 are shown as absolute value address data 122 in FIG. 21.

The outputs of the absolute value circuits 1205 and 1206 serve as read addresses of the correction ROM 13C and data output from the ROM 13C provides the address for reading the image memory 5 serving as rear image storage means.

That is, the address absolute values (2, 2) shown in a picture 122a in the absolute value address data 122 in FIG. 21 provides the address of the ROM 13C and corrected address data (1, 1) stored in the address (2, 2) is converted as the address data of a picture element 123a in an image area 123 in FIG. 21. Each of other addresses shown in the address data 123 in FIG. 21 is obtained by writing the above address in each picture element.

At this point of time, influences of taking absolute values to read data from the ROM 13C and subtracting the central coordinates are left. Therefore, inverse operation is applied to the data read out of the ROM 13C. First, signals are changed in accordance with sign decision signals HC0 and VC0 output from the subtracters 1203 and 1204 by sign changers 1207 and 1208.

Address data 124 in FIG. 21 shows the sign change state.

Moreover, outputs of the sign changers 1207 and 1208 are input to adders 1209 and 1210 to add central coordinates 1211 and 1212. This result provides the address for reading the image memory 5 storing the image data captured by the CCD 2.

The data serves as address data 125 corresponding to the image memory in FIG. 21.

In the case of the above-described image processor 30C of this embodiment, the capacity of the ROM 13C for storing corrected values requires only ¼ the capacity of the ROM of the first embodiment. Therefore, the circuit scale is decreased and the processor cost can be decreased.

For the correction by the image processor 30C of this embodiment, it is also possible to realize a modified image processor using the correction method applied to the first embodiment for correcting an optical distortion of an image at the central portion of an image area and preventing an image at the marginal portion of the image area from going out of the image area.

As the corrected address data of the fourth quadrant stored in the correction ROM of the modified image processor, data for correcting an optical distortion is stored in the area enclosed by horizontal and vertical axes passing through the optical axis center O and a ¼-circumference circular arc with a radius X0 and data for correcting captured image data so that the data does not protrude from a corrected image area is stored in the area between the circular arc and the image area end.

By adding moving distances Δx and Δy to outputs of the adders 1209 and 1210 respectively, it is possible to move an image and display an image with its optical distortion corrected on any position of a monitor. Moreover, by synchronizing a moving distance with a hand displacement of an apparatus such as a video camera, it is possible to correct an optical distortion while correcting the hand displacement. Furthermore, by making the H central coordinate 1211 and V central coordinate 1212 variable, it is possible to shift the center of correction, align the center of a correction characteristic with the optical axis center, and eliminate a correction error. Furthermore, it is possible to omit complex design for aligning the optical axis of the image pickup lens 1 with the center of the CCD 2 and mechanical adjustment requiring a cost, and decrease the cost of a system.

It is also possible to set an operating button on the processor so that a user can operate an operational section 14E for designating the above central coordinate values X and Y or to set the button in the processor so that an adjuster can operate the button only to designate the values.

Moreover, when a lens characteristic changes depending on a focal distance like, for example, a zoom lens, selecting a plurality of ROMs storing correction characteristics suitable for focal distances can be applied to a case of using an image pickup lens whose distortion characteristic changes like a zoom lens and the correction accuracy is improved.

Furthermore, because the lens 1 and the correction ROM 13C are removable from the processor 30C, the lens 1 can be replaced with a lens 1 with a different imaging characteristic and, in this case, correction suitable for the characteristic of the replaced lens 1 can be made by a ROM 13C which is simultaneously replaced with the above ROM 13C.

Furthermore, by integrating the ROM storing the correction characteristics and serving as processing-information storage means with an exchange lens, the operating condition is further improved when a camera is used as an image processor.

Then, the third embodiment of the present invention is described below. For example, the first embodiment or its modification stores correction characteristics in the ROM 13B and ROM 13B'. Therefore, when, for example, the lens 1, objective system 51, or imaging lens system 54 is constituted with a zoom lens system and optical distortion characteristics are changed due to focal distances, ROMs equal to the number of the optical distortion characteristics are required and thereby, the circuit scale is increased.

Therefore, it is an object of the third embodiment to provide an image processor having a structure capable of corresponding to the above case without increasing the circuit scale. The third embodiment is described below by referring to the accompanying drawings.

FIG. 22 is a block diagram showing the structure of an image processor or an image pickup device for correcting an optical distortion. In FIG. 22, a component provided with a symbol same as that in FIG. 8 has the same function as the component in FIG. 8.

An image processor 30H in FIG. 22 forms an enlarged or contracted image on the image pickup surface 2A of the CCD 2 by a zoom lens system 1'. The zoom lens system 1' is driven by, for example, a zoom driving circuit 25 provided with a motor and thereby, imaging magnifications (zoom magnifications) change.

Moreover, the processor 30H has a personal computer 11H. When inputting data for designating a zoom magnification through a keyboard 26, the personal computer 11H outputs zoom information equivalent to the zoom magnification to the zoom driving circuit 25. The zoom driving circuit 25 drives the zoom lens system 1' to set the system 1' to a designated zoom-magnification state.

Moreover, the personal computer 11H controls the zoom lens system 1' as described above and also transmits a zoom coefficient Sa showing zoom information and coefficients Sb and Tb necessary for switching of characteristics for correction of central and marginal portions to a read control circuit 12H. The read control 12H transmits address signals for performing corrections for optical distortion and protrusion prevention to the image memory 5 and interpolation circuit 6.

FIG. 23A shows an optical distortion characteristic about the relation between relative distance (%) from the optical axis and distortion factor D (%) in the zoom lens system 1'. In this case, the horizontal axis represents the relative distance from the optical axis position when assuming the length ½ the diagonal line of the effective surface of the image pickup device (CCD 2) as 100% and the vertical axis represents the distortion factor D. In this case, if an image to be formed at a point separated by a relative distance r is formed at a position r' due to an optical distortion, the distortion factor D is defined by the following expression 1 as shown in FIG. 23B.

$$D=(r-r')/r \times 100(\%) \quad \text{(Expression 1)}$$

Though a characteristic is fluctuated due to a focal distance f, the absolute value of the distortion factor D also increases as r increases. The characteristic can be approximated by the following expression 2.

$$D=s'' \times sq(r) \quad \text{(Expression 2)}$$

From (Expression 1) and (Expression 2), the following expression 3 is obtained.

$$r'=r \times (1+s' \times sq(r)) \quad \text{(Expression 3)}$$

In this case, because sq (r) represents the square of r and s" and s' are coefficients to be determined by a focal distance, the following expression 4 is effected.

$$s'=s''/100 \quad \text{(Expression 4)}$$

That is, from Expression 3, it can be concluded that an image to be formed at a point separate by the relative distance r from the optical axis of an image pickup device is formed at a point separate by $(1+x' \times sq(r))$ times the distance r due to an optical distortion.

A point p separate by the relative distance r from the optical axis of the image pickup device is assumed on an image memory. In this case, as shown in FIG. 24, the point p is shown by a small letter on the image pickup device and by a capital letter on the image memory which can be regarded to be equivalent as shown by an equal sign.

Figure 25B:
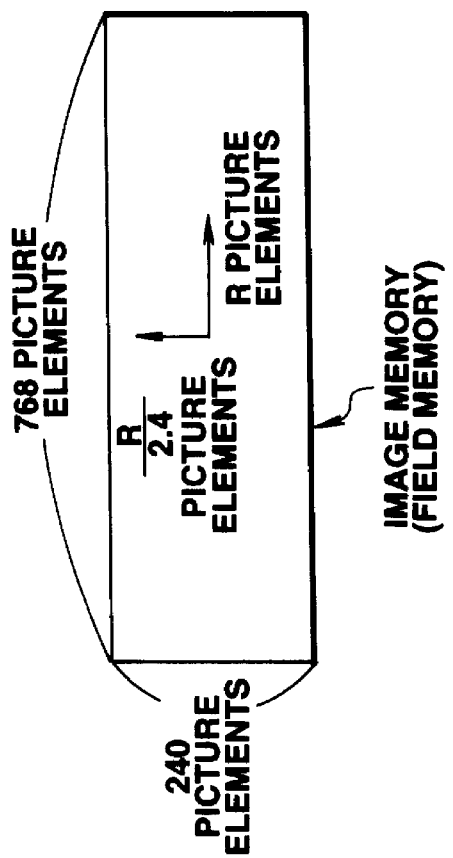
FIGS. 25A and 25B are illustrations showing the aspect ratio of an image pickup device and the relation between the number of picture elements in the horizontal direction and the number of picture elements in the vertical direction on a field memory.
Figure 25A:
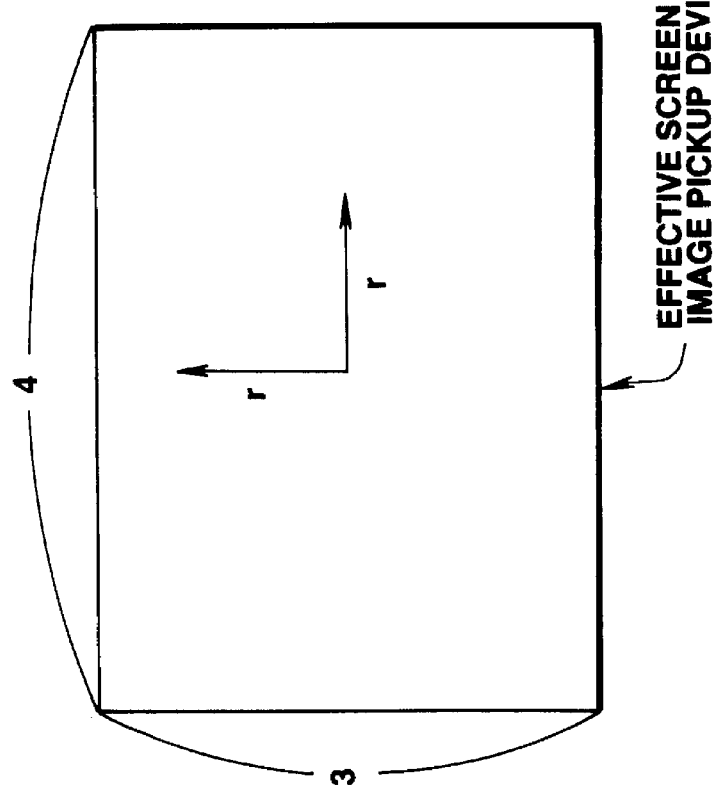

As shown in FIG. 25A, the aspect ratio of the image pickup device is approx. 3:4 in the case of an NTSC signal. When storing this picture signal in an image memory using a field memory of 240×768 as shown in FIG. 25B, the relative distance r on the image pickup device comes to R/2.4 picture elements in the vertical direction if the distance r corresponds to R picture elements in the horizontal direction on the image memory. Thus, the distance r is shown in different number of picture elements in the horizontal and vertical directions. Therefore, in the case of this example, the number of picture elements in the vertical direction is multiplied by a scaling factor k such as 2.4 so that the relative distance r on the image pickup device can be converted into the number of picture elements of the image memory such as R picture elements for both horizontal and vertical directions.

In this case, as shown in FIG. 24, a case is assumed in which a point to be imaged at the point p separate by the relative distance r from the optical axis of the image pickup device is imaged at a point p' separate by the relative distance r' from the optical axis due to an optical distortion. When assuming that the point p is located at a position separate by x picture elements in the horizontal direction and y picture elements in the vertical direction from the central coordinates of the image memory corresponding to the optical axis of the image pickup device and the point p' is located at a position separate by x' picture elements in the horizontal direction and y' picture elements in the vertical direction from the central coordinates, the positional relation between P and P' corresponding to the points p and p' respectively on the image memory are obtained.

From (Expression 3), it is considered that the point p' is located at a position $\{1+s' \times sq(r))$ times farther than the point p from the central coordinates. In this case, the distance r is shown by the following expression 5 in terms of a size on the image memory by assuming that X=cx corresponds to Y=cky.

$$R=\sqrt{(sq(X)+sq(Y))}=c \times \sqrt{\{sq(x)+sq(k \times y)\}} \quad \text{(Expression 5)}$$

In the above expression, symbol $\sqrt{( \ldots )}$ or $\sqrt{\{ \ldots \}}$ represents the square root of ( ... ) and c represents a constant determined by the size of the image pickup device and the number of picture elements of the image memory. Moreover, that the point p' is located at a position (1+s'×sq(r)) times farther than the point p from the central coordinates represents that the distances of the point p' from the central coordinates in the horizontal and vertical directions are also (1+s'×sq(r)) times larger than those of the point p. Therefore, the following expressions 6 and 7 are obtained.

$$x'=x \times (1+s' \times sq(r)) \quad \text{(Expression 6)}$$

$$y'=y \times (1+s' \times sq(r)) \quad \text{(Expression 7)}$$

Thus, from (Expression 5), (Expression 6), and (Expression 7), the following expressions 8 and 9 are obtained.

$$X'=X \times [1+s' \times sq(c) \times \{sq(X)+sq(k \times Y)\}] \quad \text{(Expression 8)}$$

$$Y'=Y \times [1+s' \times sq(c) \times \{sq(X)+sq(k \times Y)\}] \quad \text{(Expression 9)}$$

In this case, by substituting a constant S for (s'×sq(c)) the following expressions 10 and 11 are obtained.

$$X'=X \times [1+S \times \{sq(X)+sq(k \times Y)\}] \quad \text{(Expression 10)}$$

$$Y'=Y \times [1+S \times \{sq(X)+sq(k \times Y)\}] \quad \text{(Expression 11)}$$

Moreover, the constant S is a coefficient determined by a focal distance f.

The above expressions show that image data to be stored in a picture element P (X, Y) which is X and Y separate from the central coordinates of the image memory in the horizontal and vertical directions is stored at the point P' (X', Y') separate from the central coordinates of X' and Y' which are [1−s×{sq(X)+sq(k×Y)}] times larger than X and Y respectively due to an optical distortion. Therefore, an optical distortion is corrected by reading image data stored at the point P' at the timing for reading the point P when reading the image data from the image memory.

In the above description, when expressing the distance r from the optical axis of the image pickup device in terms of picture elements X and Y of the image memory, the square root operation such as R=√(sq(X)+sq(Y)) is used in accordance with the Pythagorean theorem. In the case of this embodiment, however, the square root operation and the square operation are offset each other and the scale of the operation circuit is decreased because the optical distortion characteristic is approximated to D=s"×sq(r) as shown by (Expression 2). This is very effective because the square root operation particularly requires a large circuit scale.

Figure 26B:
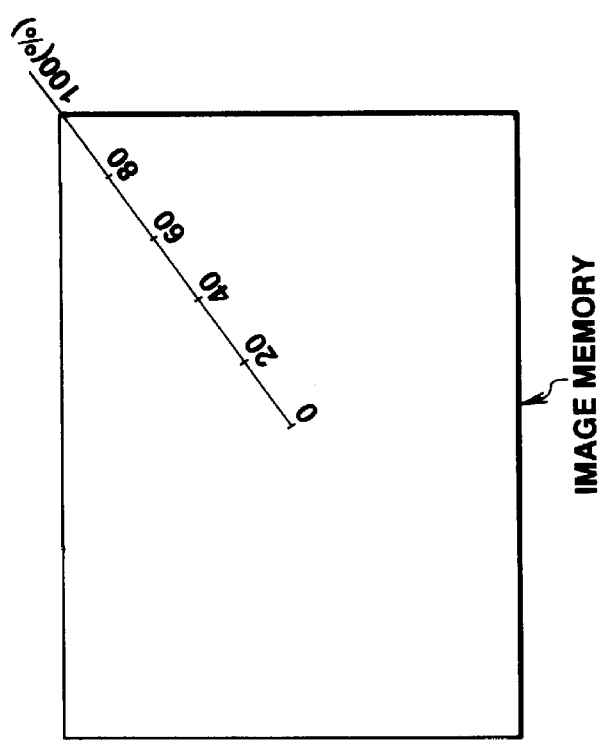
FIGS. 26A and 26B are illustrations showing the read timing characteristic shown by the horizontal axis corresponding to the read position on the vertical axis and showing the horizontal axis on an image memory.
Figure 26A:
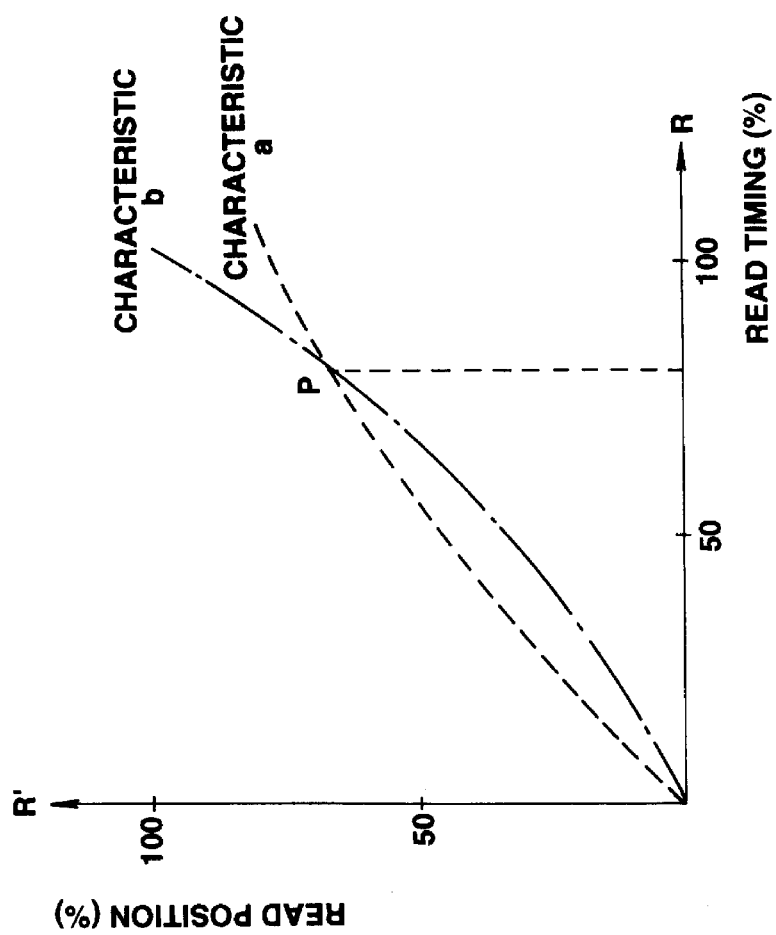

FIG. 26A shows correction characteristics of this embodiment. The horizontal axis R shows the read timing when assuming the length ½ the diagonal line of the image memory as 100 (%) as shown in FIG. 26B and the vertical axis R' shows the read position. The characteristic a is a first characteristic for correcting the above optical distortion.

For example, at the timing for reading the distance 100 (%) from the center, image data at the position of 80 (%) from the center is read. The characteristic b is a second characteristic for preventing an effective picture portion from going out of an image area size. In the case of the example shown in FIG. 26A, the characteristic b prevents the effective picture portion from going out of the screen size by performing correction opposite to the correction for reducing a distortion aberration such as a barrel or pincushion distortion by the characteristic a.

When expressing the first characteristic a by the following expression 12, $$R'=R\times(1+Sa\times sq(R)) \qquad \text{(Expression 12)}$$

the second characteristic b can be expressed by, for example, the following expression 13 which is an approximate expression very similar to the first characteristic.

$$R'=R'\times(T+Sb\times sq(R)) \qquad \text{(Expression 13)}$$

In the expression 13, T represents a coefficient to be determined by values of Sa, Sb, and P, which is 1 or less.

By exchanging these two characteristics a and b at the point P where the characteristics intersect each other as shown in FIG. 26A, it is possible to perform the first correction for correcting a distortion at the central portion of an image and the second correction for preventing an effective picture portion from going out of the screen size at the marginal portion of the image. Correction expressions are summarized as shown below.

In the case of the distance from the center $0 \leq c\sqrt{\{sq(X)+sq(k\times Y)\}} < P$ (hereafter referred to as area a), the following expressions 14 are effected.

$$X'=X\times[1+Sa\times\{sq(X)+sq(k\times Y)\}] \qquad \text{(Expression 14)}$$

$$Y'=Y\times[1+Sa\times\{sq(X)+sq(k\times Y)\}] \qquad \text{(Expression 14)}$$

In the case of the distance from the center $P \leq c\sqrt{\{sq(X)+sq(k\times Y)\}}$ (hereafter referred to as area b), the following expressions 14 are effected.

$$X'=X\times[Tb+Sbx\{fsq(X)+sq(k\times Y)\}] \qquad \text{(Expression 14)}$$

$$Y'=Y\times[Tb+Sbx\{fsq(X)+sq(k\times Y)\}] \qquad \text{(Expression 14)}$$

FIG. 27A shows an example of the read control circuit 12H of this embodiment. In FIG. 27A, an H start address generation circuit 61 and a V address generation circuit 63 are circuits for generating a processing start address. This embodiment generates "0" as a start address (HST in the case of the H start address generation circuit 61 and VST in the case of the V address generation circuit 63) and these addresses are latched by latched circuits 65 and 67.

An H address pitch generation circuit 62 and a V address pitch generation circuit 64 are circuits for generating an address pitch. This embodiment generates "1" as a pitch (HP in the case of the H address pitch generation circuit 62 and VP in the case of the V address pitch generation circuit 64) and these pitches are latched by latched circuits 66 and 68. The latched circuits 65, 66, 67, and 68 operate in response to a vertical (V) synchronizing pulse and data read out of each latched circuit is supplied to one input terminal of each of a selection circuit 69, an adder 71, a selection circuit 70, and an adder 72 respectively comprising a change-over switch.

Outputs of the adders 71 and 72 are supplied to the other input terminals of the selection circuits 69 and 70 for switching and outputting the outputs in response to a horizontal (H) synchronizing pulse and a V synchronizing pulse. That is, the selection circuits 69 and 70 output data through the latched circuits 65 and 67 at the time of start, and switch and output the data from the adders 71 and 72 from the next address.

The outputs of the selection circuits 69 and 70 are latched by latched circuits 73 and 74 respectively, and latched outputs are supplied as other inputs of the adders in response to a clock and an H synchronizing pulse respectively and output to an origin-moving block circuit 75 at the rear stage.

The above structure generates a horizontal-directional read timing address and a vertical-directional read timing address. The read timing address for reading the image memory 5 is read from top left to bottom right similarly to scanning of a television. When the coordinate system at the time of outputs of the latched circuits 73 and 74 is set as shown in FIG. 27B, the top left comes to the origin (0, 0), the bottom left comes to (2X0, 2Y0), and the center comes to (X0, Y0).

Though the central coordinate of the image memory 5 is set to the origin in the case of (Expression 14), the top left is the origin in the case of the read timing address as shown in FIG. 27B. Therefore, it is necessary to move the origin so that this supplied address serves as the information for the distance from the central coordinate address (X0, Y0).

The origin-moving block circuit 75 executes the above origin moving and comprises subtraction circuits 76 and 77 for subtracting the central value address (X0, Y0) from a timing address value. As the result of the origin moving, the coordinate system shown in FIG. 27C is obtained. Outputs of the subtraction circuits 76 and 77 are input to a distance operation block 78.

Then, the distance operation block 78 executes $\{sq(X)+sq(k\times Y)\}$ in (Expression 14). An input signal corresponding to X is squared by a multiplier 79 and thereafter, input to an adder 80. An input signal corresponding to Y is multiplied by a conversion factor k in a multiplier 81 and thereafter, squared by a multiplier 82. Outputs of the multipliers 79 and 82 are added each other by the adder 80 and input to a distortion-magnification operation block 83.

The distortion-magnification operation block 83 is a circuit for computing $[T+S\times\{squ(X)+sq(k\times Y)\}]$ in (Expression 14). In this expression $[T+S\times\{squ(X)+sq(k\times Y)\}]$, factors T and S represent distances $\{sq(X)+sq(k\times Y)\}$ from the center, and 1 or Tb is selected as T and Sa or Sb is selected as S. Sa, Sb, and Tb are factors supplied from the personal computer 11H, Sa is a focal-distance factor determined by a focal distance f of a zoom lens, and Sb and Tb are factors determined by characteristic exchange timing.

The exchange timing inputs $\{sq(X)+sq(k\times Y)\}$ supplied from the distance operation block 78 to a comparator 84, decides whether an area is the above a or b, and supplies a decision result to selection circuits 85 and 86. The selection circuit 85 outputs Sa to the multiplier 87 when the area is decided as a but outputs Sb to the multiplier 87 when the area is decided as b, and the selection circuit 86 outputs "1" to the adder 88 when the area is decided as a but outputs Tb to the adder 88 when the area is decided as b.

The expression $\{sq(X)+sq(k\times Y)\}$ supplied from the distance operation block 78 is multiplied by S supplied from the selection circuit 85 in the multiplier 87, and an output of the selection circuit 86 is added to the multiplication result and the addition result is output to X' and Y' operation block 89 at the next stage.

X' and Y' in (Expression 14) are obtained by multipliers 91 and 92 constituting the X' and Y' operation block 89. The multipliers 91 and 92 multiply an output of the adder 88 by X and Y output from the subtracters 76 and 77 respectively and output signals corresponding to X' and Y' to an origin-moving block 93 at the next stage.

X' and Y' thus obtained represent the address of the XY coordinates when using the center as the origin as shown in FIG. 27C and the actual origin of the image memory is located at the top left as previously described. Therefore, by adding X' and Y' central coordinate address values each other in the adders 94 and 95 of the origin-moving block 93, the coordinates are returned as shown in FIG. 27D.

Through the above processing, the read address of the first correction corresponding to the distortion of an image is generated at the central portion of the image and the read address of the second correction for preventing an effective picture portion from going out of the screen size is generated is generated at the marginal portion of the image. By reading the image memory 5 with these read addresses Xa and Ya, the first correction corresponding to the distortion of the image is performed at the central portion of the image and the second correction for preventing the effective picture portion from going out of the screen size is performed at the marginal portion of the image.

This embodiment makes it possible to correspond to any optical distortion of a lens only by changing factors in an expression because an optical distortion is approximated by the expression. Moreover, the above-described optical distortion characteristic can be approximated by various expressions. It is described that correction is mainly performed by a term up to the second order of the distance r in the above case. However, by performing approximation up to a higher-order term such as approximation of a distortion aberration by a multinomial with a cubic or quartic term, approximation can be made at a higher accuracy and a higher-order correction is realized.

In the above description, an optical distortion is corrected through read control of the image memory 5. However, it is a matter of course to correct the optical distortion through write control of the image memory 5. That is, it is possible to perform correction through at least one of the read operation control and write operation control of the image memory 5.

When applying the processor 30H in FIG. 22 to the endoscope system 31 in FIG. 13 or 14, the lens 1' represents the objective system 51, relay lens system 52, eyepiece system 53, and imaging lens 54. In this case, a case of only performing distortion correction by a lens system with the largest distortion aberration (e.g. the objective system 51) is also included. Moreover, it is possible to constitute the structure shown in FIG. 22 by using the components shown in FIG. 14.

Moreover, making the central coordinates (X0, Y0) variable is convenient because it is possible to move the center of correction and moreover decrease the cost required for adjustment of the positional relation between the lens 1' and an image pickup device such as the CCD 2 because correction can electrically be made even if the accuracy of the positional relation between the lens 1' and the image pickup device is low and the optical axis does not coincide with the center of the image pickup device.

Furthermore, an image can be moved by making the H start address and V start address variable or the image can be enlarged or contracted by making the H address pitch and V address pitch variable. Making the H and V start addresses variable or making the H and V address pitches variable is convenient particularly when correcting an optical distortion of an image displayed on a color monitor of medical equipment by moving an endoscope image displayed at a position other than the center of the image such as the top left of the image to the center of a screen. The advantage that enlargement and contraction of an image and optical distortion correction of the image can be performed at the same time includes the following.

Figure 28A:
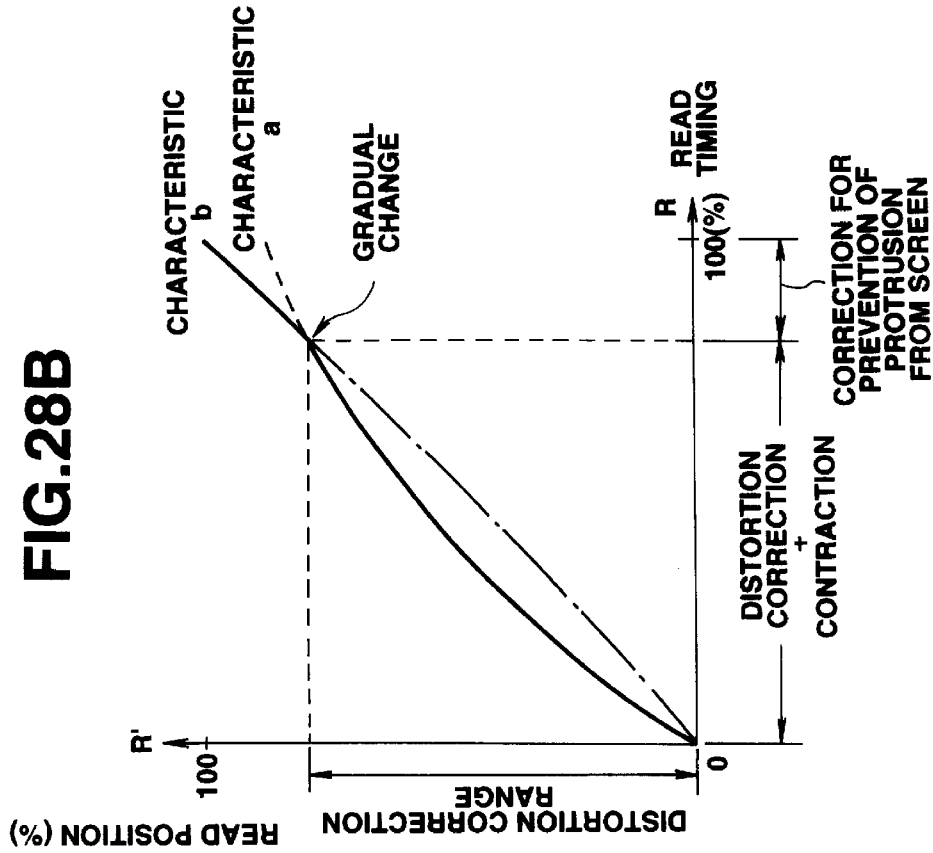
FIGS. 28A and 28B are illustrations for explaining that a characteristic becomes steep at a boundary point when the central area is widened only by distortion correction and characteristic change can be moderated at the boundary point by performing contraction together with distortion correction.
Figure 28B:
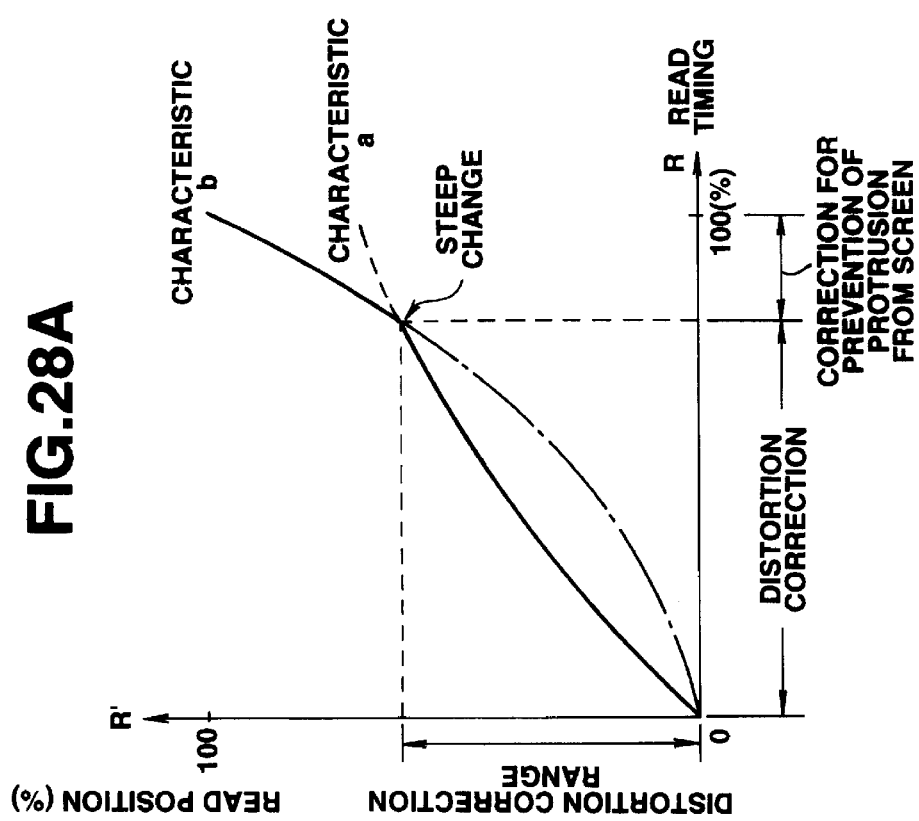

For an exchange point of the above areas a and b (e.g. the point P in FIG. 26A), further increasing the area a is better because the range for correcting an optical distortion increases. However, as shown in FIG. 28A, if the range of the area a is expanded, the change of characteristics becomes steep at the exchange point with the area b. Therefore, as shown in FIG. 28B, by performing contraction and distortion correction of an image in the area a at the same time, there are advantages that distortion correction can be performed in a wider range on the imaging surface of an image pickup device and the change of characteristics of the areas a and b becomes gradual.

The fourth embodiment of the present invention is described below.

Though the first to third embodiments use a correction method for one determined optical system, some endoscopes have many distortions in their optical systems but some endoscopes have little distortion in their optical systems. Moreover, an endoscope uses various types of optical systems.

Figure 29:
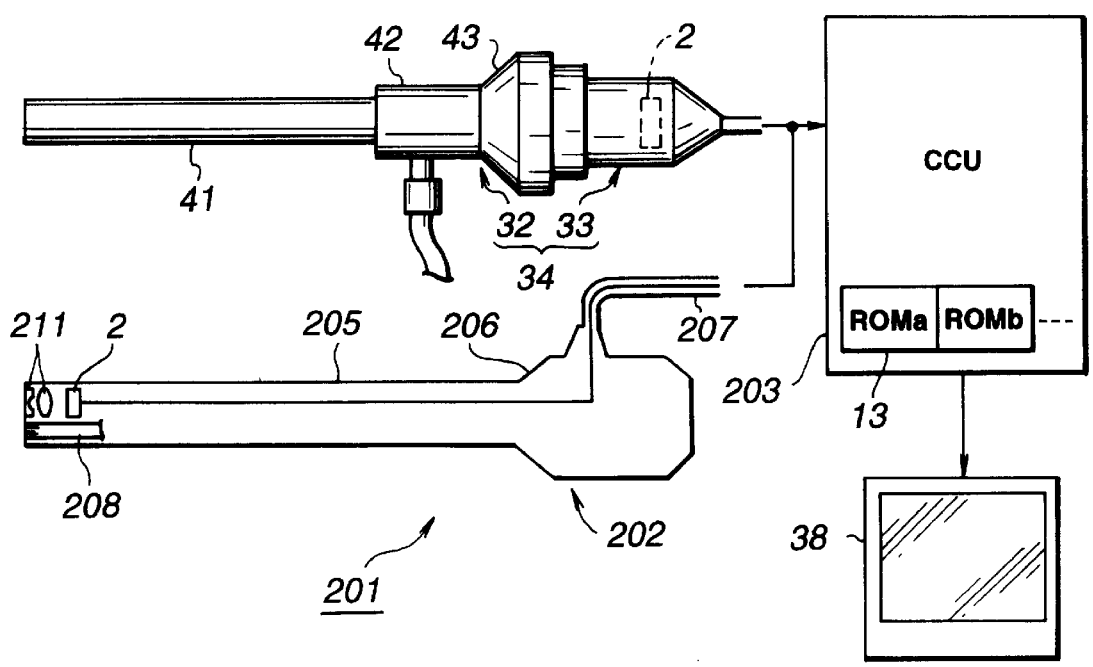
FIG. 29 is a block diagram showing the whole structure of an endoscope system provided with the fourth embodiment of the present invention.

Therefore, it is an object of this embodiment to provide an apparatus capable of performing correction for practically used endoscopes. FIG. 29 shows an endoscope 201 whose light source unit is not illustrated. The endoscope 201 has a CCU 203 for performing signal processing for the TV-camera-mounted endoscope 34 or an electronic endoscope 202 having a built-in image pickup device at its front end and a picture signal output from the CCU 203 is output to the color monitor 38.

The electronic endoscope 202 has a flexible slender inserting portion 205, an operational section 206 is formed at the rear end of the inserting portion 205, and a universal cord 207 is extended from the side of the operational section 206. A light guide 208 is inserted into the inserting portion 205 and universal cord 207, and illumination light supplied from a light source unit is transmitted by connecting a not-illustrated light-source connector set at an end of the universal cord 207 to the light source unit and emitted from its front end .

An objective system 211 for capturing an optical image of an object is set to the front end of the inserting portion 205 and the image pickup surface of the CCD 2 is arranged on the focal surface of the system 211. A cable connected to the CCD 2 is inserted into the inserting portion 205 and universal cord 207 and moreover, a signal connector set at an end of a cable extended from the light source connector can removably be connected to the CCU 203.

That is, in the case of the electronic endoscope 202, the objective system 211 and CCD 2 are built in the front end of the inserting portion 205. In the case of the TV-camera-mounted endoscope 34, e very rigid endoscope 32 is constituted with a lens system and a TV camera having the built-in CCD 2 is mounted on the eye contacting portion 43 of the endoscope 32. Because the TV-camera-mounted endoscope 34 is described in FIG. 14, the structure of it is omitted.

Moreover, a not-illustrated electronic endoscope constituted with a lens system having a characteristic different from that of the objective system 211 can also be used for endoscope inspection by connecting the endoscope to the CCU 203.

An image obtained by the CCD 2 passes through the CCU 203 and it is displayed on the color monitor 38. For example, when using a predetermined ROM or a specific factor as described above, it is impossible to correct a distortion at all when changing endoscopes. Therefore, the following structure, for example, is used so that it can correspond to any endoscope.

Figure 30:
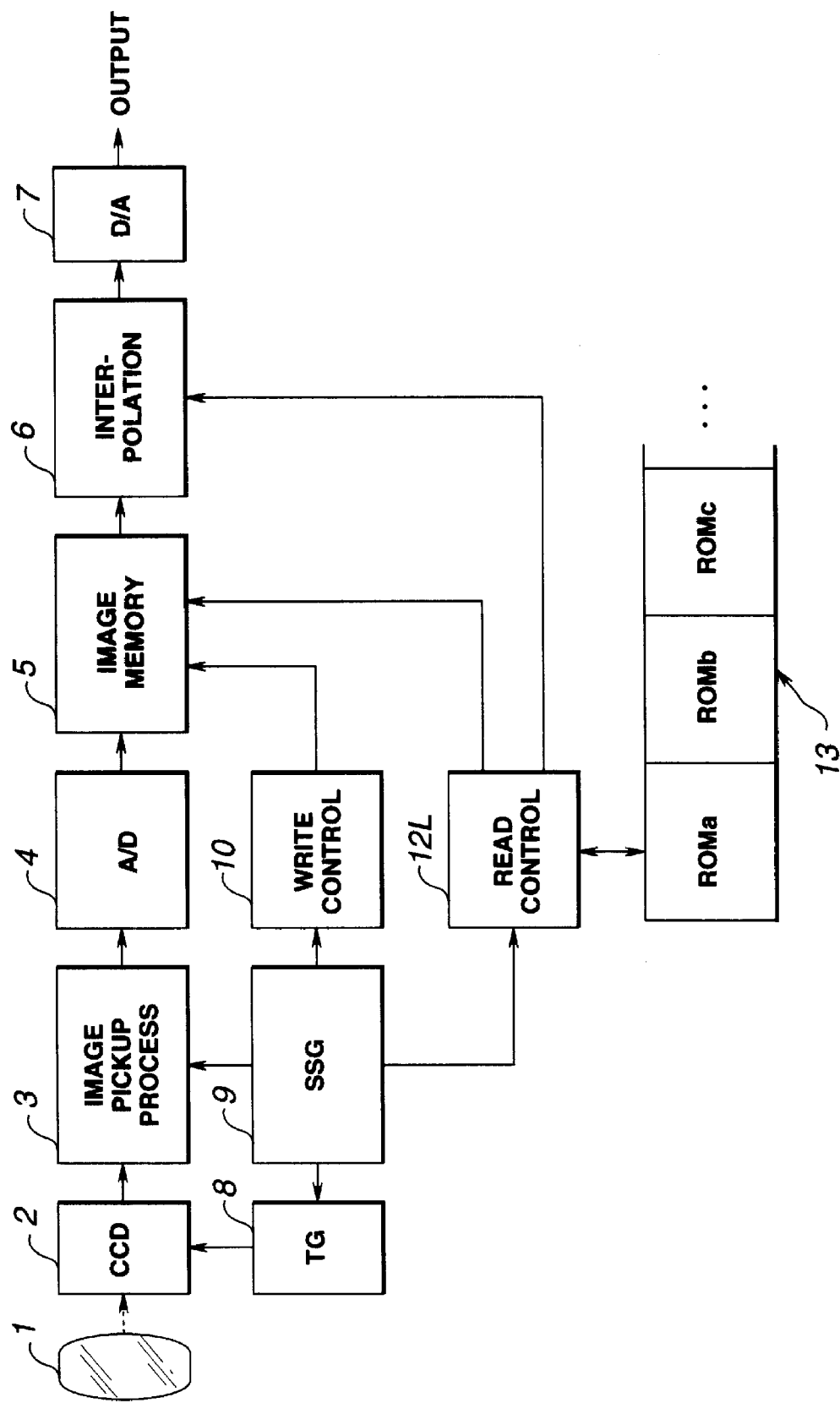
FIG. 30 is a block diagram showing the structure of the fourth embodiment of the present invention.

FIG. 30 shows the structure of the CCU 203. That is, the CCU 30 has a function for correcting a distortion of an image in addition to the CCU function for generating a normal picture signal (for example, the structure of the CCU 30 corresponds to the structure provided with the CCU 36 and image processing unit 37 in FIG. 14). Though the block structure can use the components in FIG. 14, FIG. 30 shows a structure provided with the same components as those of the first embodiment shown in FIG. 8.

This embodiment shows a block diagram for storing a corrected value in the ROM 13 and reading and using it according to the necessity similarly to the first embodiment. This embodiment is different from the first embodiment in that the ROM 13 comprises various types of ROMs such as ROMa, ROMb, ROMc, etc.

A corrected value is previously stored in each of the ROMa, ROMb, ROMc, etc. correspondingly to each endoscope (optical system) and a read control circuit 12L selectively uses the corrected information in ROMi (i=a, b, c, . . .). For example, the ROMa is used for the TV-camera-mounted endoscope 34 and the ROMb is used for the electronic endoscope 202.

When ROMi is practically used:

(a) ROMi is manually replaced in accordance with an endoscope (optical system).

(b) Each ROMi is stored in an endoscope.

(c) An endoscope is provided with scope discrimination means such as a bar code, color, connector shape, and resistance value and ROMi is automatically replaced by an output discriminated by the scope discrimination means.

As described above, this embodiment makes it possible to correct every distortion independently of presence or absence of a distortion or the position of the CCD of an endoscope because ROMi corresponding to any optical system is used.

Then, the fifth embodiment of the present invention is described below.

The fourth embodiment has a disadvantage that ROMs equal to the number of optical distortion characteristics are necessary and the scale is increased when the characteristics are changed due to the focal distance of a zoom lens or the like, similarly to the first embodiment.

Therefore, a characteristic exchange point is obtained through arithmetic as described above. Change of characteristic or exchange points is executed by changing operation factors. It is an object of this embodiment to provide correction means capable of corresponding to any optical system (or any endoscope with different optical system), similarly to the fourth embodiment.

Operation factors can easily be changed by, for example, the DIP switch of the personal computer 11M. Operation factors are changed and set by the DIP switch and manually in accordance with an endoscope (optical system).

Figure 31A:
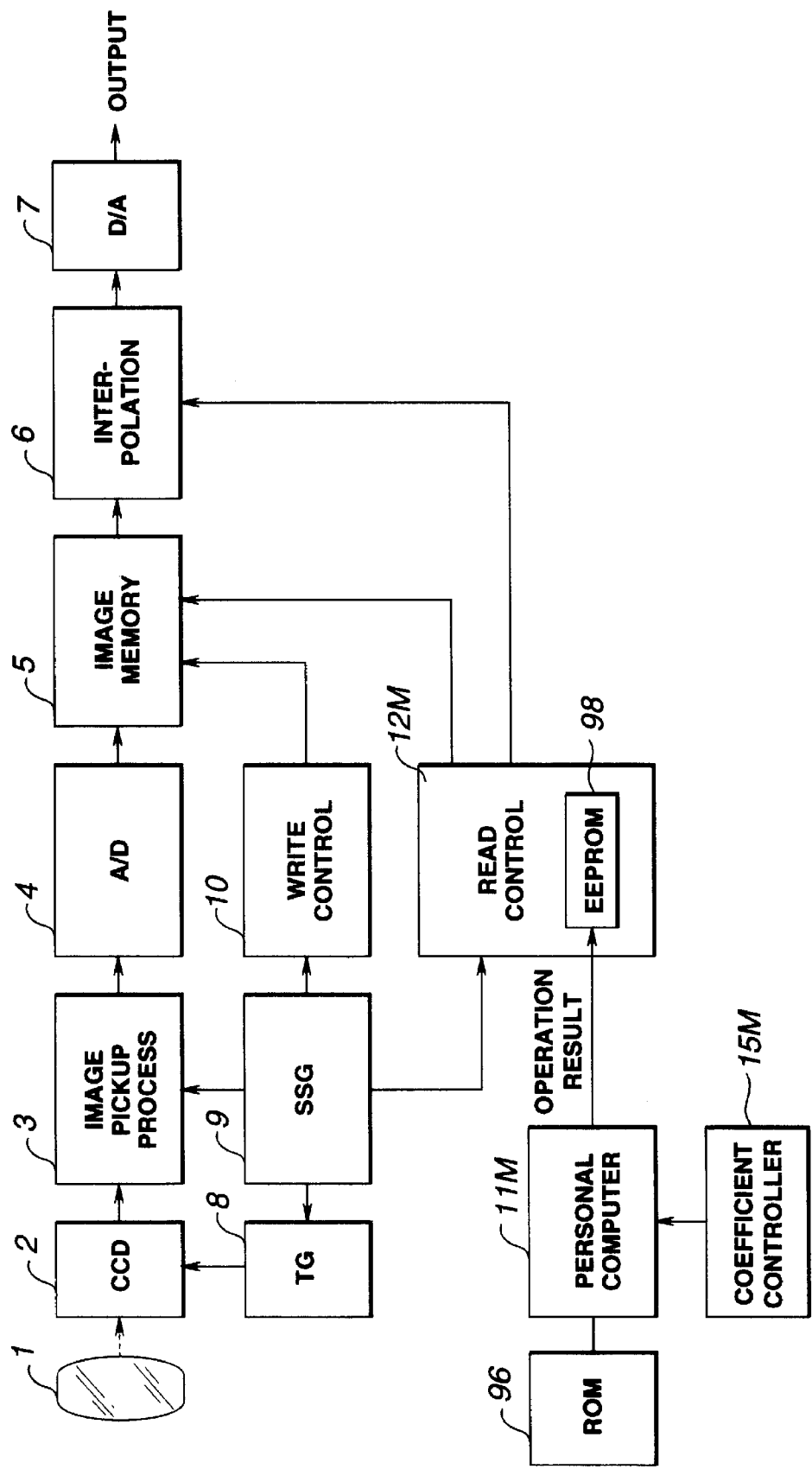
FIGS. 31A and 31B are block diagrams showing structures of the an image processor of fifth embodiment and its modification.

As shown in FIG. 31A, when inputting an endoscope name to be used to, for example, the personal computer 11M by using a factor controller 15M, the personal computer 11M refers to a ROM 96, reads the factors Sa, Sb, and Tb corresponding to the endoscope name, generates address conversion information for performing the correction of a distortion at the central portion and the correction for prevention of protrusion at the marginal portion about the optical system of the endoscope, and stores the information in an EEPROM (electrically erasable and programmable ROM) 98 included in the read control 12M. The EEPROM 98 is a nonvolatile semiconductor memory in which data is electrically rewritable.

Thus, the read control circuit 12M can display a corrected image whose distortion at the central portion can be corrected and whose protrusion from the marginal portion can be prevented on a monitor as described in the first embodiment or the like by applying read address to the EEPROM 98 to read address conversion information for performing the correction of a distortion at the central portion and the correction for prevention of protrusion at the marginal portion and applying the address conversion information to the image memory 5 to read image data.

Figure 31B:
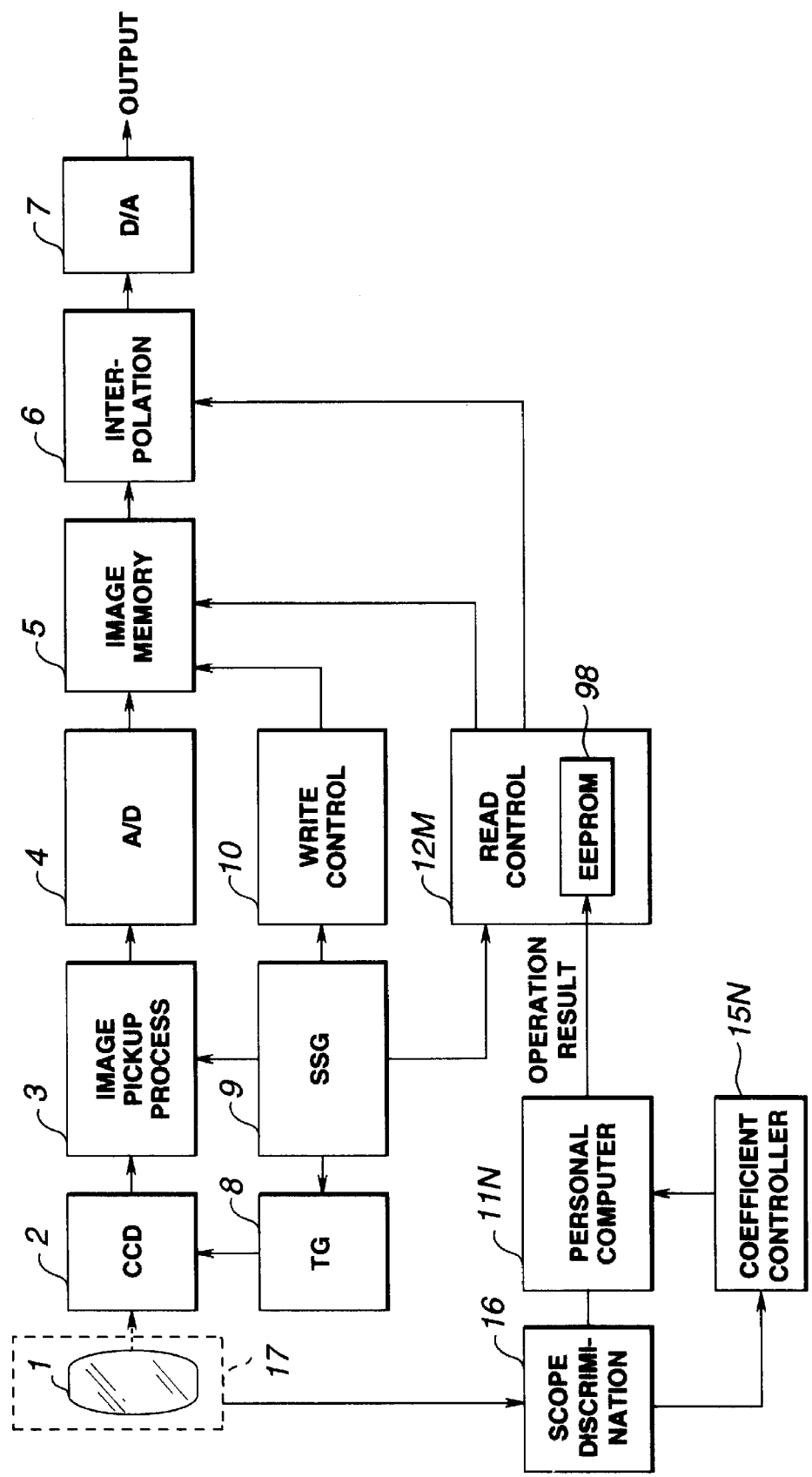

Or, as shown in FIG. 31B, a scope discrimination circuit 16 is set, the information corresponding to an endoscope 17 (or the optical system 1 used there) discriminated by the scope discrimination circuit16 is output to a factor controller 15N, the information for a corresponding endoscope name is output to a personal computer 11N from the factor controller 15N, and address conversion information is determined by the personal computer 11N and output to the EEPROM 98.

The above scope discrimination is performed by discriminating a bar code set correspondingly to a scope. Moreover, it is possible to perform scope discrimination by discriminating color, connector shape, or resistance value.

As described above, because this embodiment makes it possible to set an operation factor corresponding to any optical system, correction can be made without depending on the presence or absence of a distortion, an optical system of an endoscope, or a CCD serving as a solid image pickup device.

Then, the sixth embodiment of the present invention is described below. FIG. 32 shows the structure of an image processor 30P of this embodiment. This embodiment performs the distortion correction at the central portion and the correction for prevention of protrusion at the marginal portion of an image on the image pickup surface 2A by means of address conversion when writing image data in the image memory 5. Therefore, a write control circuit 10A reads converted address information for performing the distortion correction at the central portion and the correction for prevention of protrusion at the marginal portion by applying a normal write address to a ROM 13P storing address conversion information and stores corrected image data in the image memory 5 by applying the above address information to the address terminal of the image memory 5.

The ROM 13P can use a ROM same as the ROM 13B of the first embodiment, which performs address conversion at the time of write though the first embodiment performs address conversion at the time of read. Because image data is already corrected at the time of write, the data is read from the image memory 5 by the normal read address supplied from the read control circuit 12 and output to the D-A conversion circuit 7. Other structures of the sixth embodiment are the same as those of this embodiment and the functions and advantages of it are also the same as those of the first embodiment.

Though this embodiment is not provided with the interpolation circuit 6, it is also possible to constitute this embodiment so that it can perform interpolation.

Figure 33A:
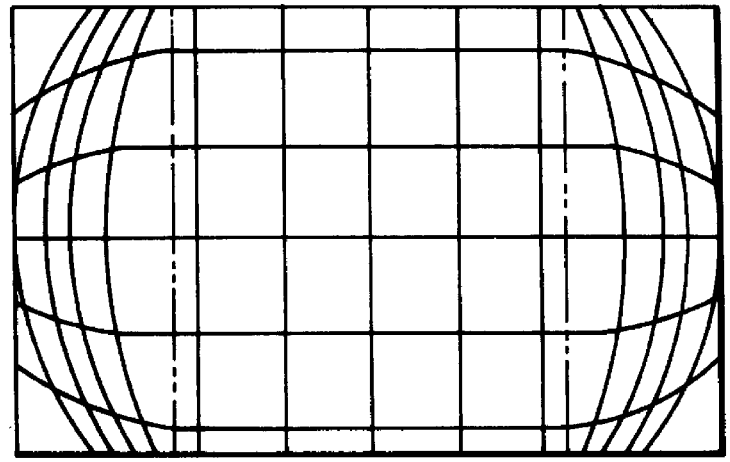
FIGS. 33A and 33B are images obtained from the seventh embodiment of the present invention and its modification.

Then, the seventh embodiment of the present invention is described below. This embodiment is constituted so as to change the horizontal- and vertical-directional correction characteristics of an image at the marginal portion. For example, when using a display unit having an oblong screen, a visual field wider in the horizontal direction can be obtained with an image of the central portion left as it is by compressing an image of the marginal portion further in the horizontal direction than in the vertical direction. FIG. 33A shows a square grid displayed on a monitor screen according to the above correction characteristic.

Moreover, when the area ratio of the central and marginal portions to the screen is optional and a resolution is required for an image at the marginal portion to a certain extent, it is possible to display the image by weakening the correction of the marginal portion compared to the above correction and contracting a distortion corrected image at the central portion. When it is enough to only recognize that any object is present as an image at the marginal portion, it is possible to further compress and display the image by further enlarging the distortion corrected image at the central portion so that the image can more clearly be observed and intensifying the correction of the marginal portion compared to the above correction.

Figure 33B:
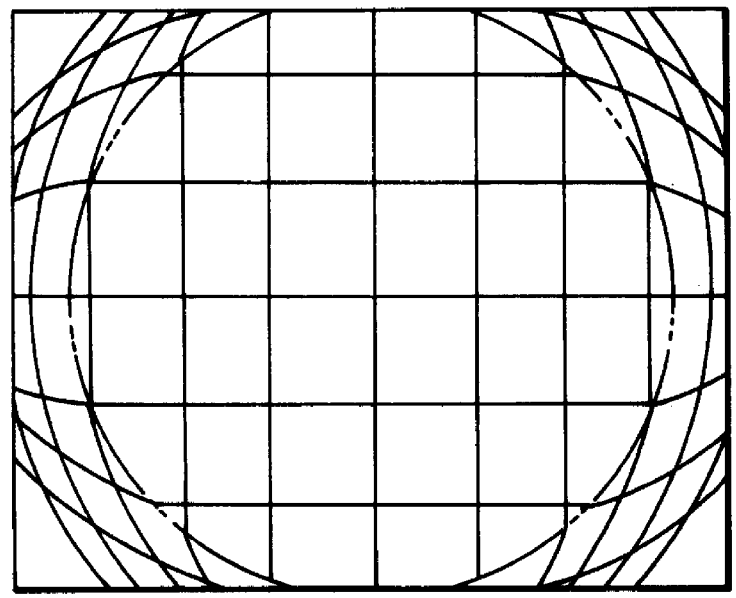

FIG. 33B shows a square grid displayed on a monitor screen according to the above case. The two-dot chain line in FIG. 33B shows a boundary.

Figure 34A:
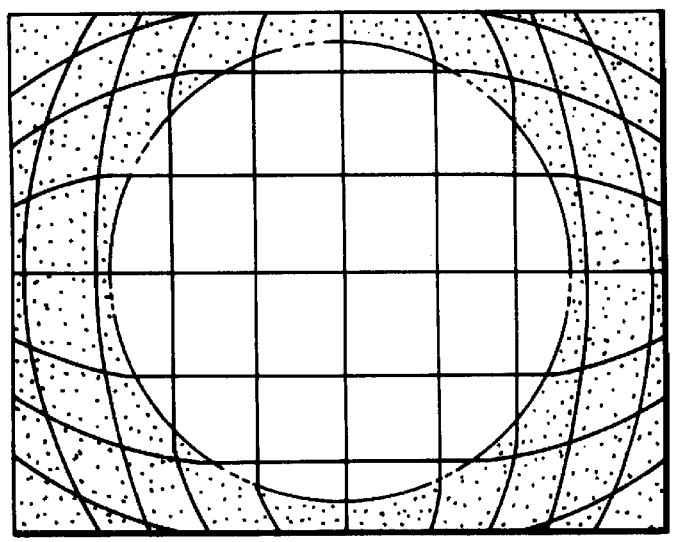
FIGS. 34A and 34B are images obtained from the eighth embodiment of the present invention and its modification.

When making a forceps approach an operating portion, the forceps is distortedly seen at the boundary of a correction characteristic depending on the inserting position of the forceps. Moreover, when the front end of the forceps is present at the marginal portion, an unexpected difference occurs in the sense of an operating surgeon when the forceps enters the central portion. Therefore, to clarify the boundary between the marginal and central portions, it is also possible to decrease the luminance or brightness of the image at the marginal portion, change the color tone, or display the boundary of the correction characteristic on the image. FIG. 34A shows a square grid displayed on a monitor screen according to the correction characteristic. In FIG. 34A, the translucent portion outside of the boundary shown by a two-dot chain line is displayed by decreasing the luminance or changing the color tone.

Moreover, in the case of the correction characteristic shown in FIG. 34A, though optical-distortion correction of the central portion is performed by further enlarging the image as it goes away from the center, it is also possible to avoid the resolution of the central portion from decreasing by further contracting the image as it approaches the center and thereby, correcting the optical distortion.

Furthermore, it is possible to perform distortion correction by combining enlargement and contraction. For example, it is possible to correct the optical distortion of an image in an area in which correction of the central portion of the image is performed closely to the corrected center by further contracting the image as it approaches the corrected center and correct the optical distortion of an image out of the area close to the corrected center by further enlarging the image as it goes away from the corrected center. In this case, a corrected image is obtained which has a proper picture-element size considering the size of the area of the central portion.

Figure 34B:
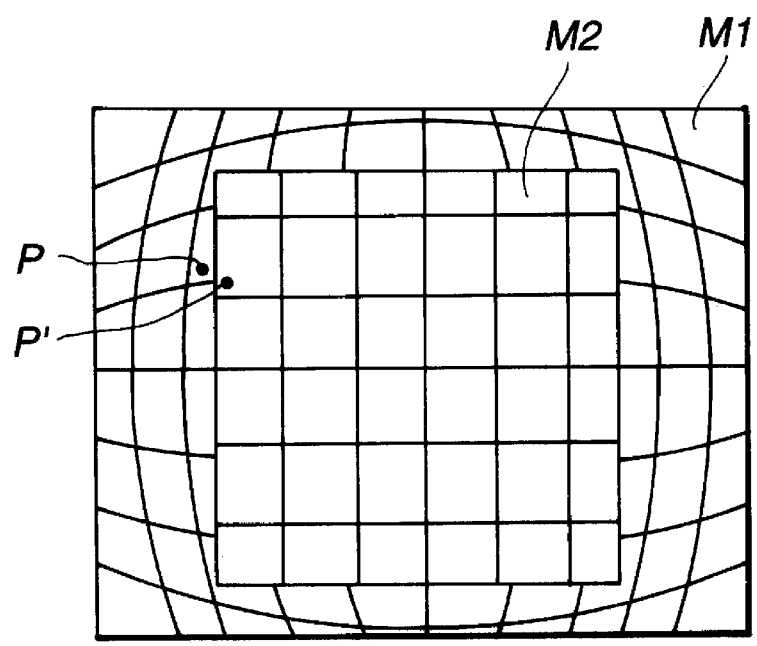

Moreover, as shown in FIG. 34B, it is possible to display a distortion-corrected image area M2 which has an image area properly smaller than the image area M1 of an original image and whose central-portion distortion is corrected so as to superimpose the area M2 on the image area M1 (for example, displaying the area M2 like a window in a computer image area) so that an operating surgeon can more easily understand the difference of correction by preventing the image areas M1 and M2 from continuing. In this case, it is necessary that only the image area M1 of the original image can be displayed correspondingly to the situation.

Furthermore, when the front end (P' in FIG. 34B) of a forceps can be seen from the image area M2 before the front end (P in FIG. 34B) of the forceps approaching from the marginal portion reaches the boundary between the image areas M1 and M2 on the image area before starting the above correction, the operating surgeon does not feel uneasiness. Therefore, to enlarge the image area M2, it is also possible to correct the image area M1 so that the distortion of the area M1 is intensified when enlarging the image area M2 and leave the image area M1 as an original image or form the area M1 into an image whose distortion is slightly corrected.

It is convenient to change corrections or original images with a switch set in an endoscope or a switch set at operating-surgeon's feet or that an original image appears when a forceps is detected and the front end of the forceps is present at the margin and the original image is changed to a corrected image area when the forceps reaches the central concerned area.

Moreover, by displaying a range serving as a corrected area when correction is applied on the image area of an original image with a frame or t he like, an operating surgeon does not loose his bearings because the difference before and after correction can easily be understood. Furthermore, it is possible to three-dimensionally observe at least the central portion and two-dimensionally observe the marginal portion by using the telescopic vision technique.

Furthermore, it is possible to automatically move an image or the corrected center by detecting the front end of a forceps with a sensor.

Though it is described in the above embodiments that correction is performed so as to prevent protrusion at the marginal portion, there are some cases in which a slight protrusion is permitted. Therefore, it is also possible that the degree of protrusion can selectively set in accordance with the necessity or selection of an user.

Moreover, an embodiment constituted by locally combining the above described embodiments is also included in the present invention.

What is claimed is:

1. An image processor comprising:

a first correcting section for performing electrical correction of distortion according to a first correction characteristic of an optical system in a first closed area at the central side in an image area set correspondingly to an image pickup surface of an image pickup device for an electrical image generated as a result of the fact that an optical image formed on said image pickup surface of said image pickup device by said optical system is photoelectrically converted by said image pickup device, said electrical correction of distortion being performed according to said first correction characteristic so that the image in said first closed area may be enlarged; and a second correcting section for performing electrical correction of distortion according to a second correction characteristic for said electrical image in a second closed area at the marginal side outside of said first closed area in said image area so that said second closed area does not protrude outside of said image area, said correction being performed according to said second correction characteristic so that the image in said second closed area may be contracted.

2. The image processor according to claim 1, wherein said image area is an area equivalent to the area of said image pickup surface.

3. The image processor according to claim 1, wherein image storage means for storing image data corresponding to said image and an address conversion circuit for performing each correction when said first and second correcting sections convert address values for reading said image data from said image storage means are further included.

4. The image processor according to claim 3, wherein said address conversion circuit has an address conversion data storing section for storing address conversion data for converting said address values.

5. The image processor according to claim 4, wherein said address conversion data storing section is a ROM.

6. The image processor according to claim 1, wherein said first closed area is a circle.

7. The image processor according to claim 1, wherein said first and second correcting sections have an information storing section for storing information to correct some areas line-symmetric to the horizontal axis or vertical axis passing through the approximate center of said image area and a correction circuit for correcting other areas in said image area by using said line-symmetric characteristic and referring to said information.

8. The image processor according to claim 1, wherein said first correcting section corrects a barrel distortion.

9. The image processor according to claim 7, wherein said information storing section stores address conversion information for geometrically moving various portions of images in said first and second closed areas and said correction circuit computes said address conversion information and corrects various portions of images in said other areas.

10. The image processor according to claim 4, wherein said address conversion data storing section is removable from said image processor.

11. The image processor according to claim 10, wherein said address conversion data storing section is integrally replaced with said optical system when said optical system is replaceable.

12. The image processor according to claim 7, wherein said information storing section stores address conversion information for correction and said correction circuit has an addition circuit for adding a predetermined offset value to a computed address by referring to address conversion information when each picture element to be processed is spatially moved and corrected.

13. The image processor according to claim 7, wherein a moving circuit is included which makes it possible to optionally move the horizontal axis and/or the vertical axis passing through the center of said image area vertically and/or horizontally.

14. The image processor according to claim 1, wherein said first and second correcting sections perform corrections corresponding to imaging characteristics of said optical system when the imaging characteristics of said optical system can be changed.

15. The image processor according to claim 1, wherein a processing information holding section for dividing said image captured by said image pickup device into four areas of top, bottom, right, and left and holding processing information necessary for the processing for correction of images in at least one of the four areas is included and the whole image is corrected by obtaining the processing information for images in three remaining areas from the processing information stored in said processing-information holding section by means of arithmetic.

16. The image processor according to claim 1, wherein said second correcting section corrects images in said second closed area at correction degrees different in the horizontal and vertical directions.

17. The image processor according to claim 1, wherein said first correcting section corrects images in said first closed area by electrically correcting the distortion of said optical system and enlarges the whole image and said second correcting section compresses the images in said second closed area up to a degree in which only the presence of an object can be recognized.

18. The image processor according to claim 1, wherein said second correcting section processes the images in said second closed area so that the color tones of them are different from those of the images corrected by said first correcting section.

19. The image processor according to claim 1, wherein boundaries between the images corrected by said first correcting section and the images corrected by said second correcting section are displayed.

20. The image processor according to claim 1, wherein said first correcting section corrects the distortion of said optical system by further enlarging an image in said first closed area as the correcting section goes away from the center of said image.

21. The image processor according to claim 1, wherein said first correcting section corrects the distortion of said optical system by further contracting an image in said first closed area as the correcting section approaches the center of said image.

22. The image processor according to claim 1, wherein said first correcting section corrects the distortion of said optical system by further contracting the image in said first closed area as the image approaches the center of the image in an area nearby the center of it and enlarging the image as the image goes away from the center in areas other than the area nearby the center.

23. The image processor according to claim 1, wherein a second corrected image obtained by correcting a distortion of the central portion of said image or distortion corrected image is further superimposed on part of said image or a corrected image generated by said first and second correcting sections and displayed.

24. An image pickup device comprising:
   an optical system for capturing an optical image of an object;
   image pickup means for receiving the optical image captured by the optical system with its image pickup surface, converting the optical image into electric image pickup signals, and outputting the signals;
   image storage means for storing the image pickup signals output from said image pickup means;
   read and write control means for controlling the read and write operations of said image storage means; and
   correction and control means constituting said read and write control means to apply a first correction characteristic for electrically correcting the optical distortion of said optical system to an image in a first area at the central side of said image pickup surface about the center of the optical axis of said optical system and a second correction characteristic for electrically correcting an image in a second area at the marginal side of said first area so that the image does not go out of an area set correspondingly to the area of said image pickup surface by controlling at least one of the write operation and read operation of said image storage means, said correction of distortion according to said first correction characteristic being performed so that the image in said first area may be enlarged, and said correction according to said second correction characteristic being performed so that the image in said second area may be contracted.

25. The image pickup device according to claim 24, wherein said first correction characteristic is a correction for an optical distortion aberration of said optical system.

26. The image pickup device according to claim 25, wherein said correction and control means applies the first correction characteristic for decreasing said distortion aberration to the image in said first area and the second correction characteristic with a characteristic opposite to the first correction characteristic for decreasing the distortion aberration to the image in said second area.

27. The image pickup device according to claim 24, wherein the image in said second area is contracted or enlarged and output from said image storage means.

28. The image pickup device according to claim 24, wherein said correction and control means has a read pulse generating section for generating a read pulse to read image data stored in said image storage means at a predetermined cycle and a read address generating section for outputting the read address in said image storage means as a function of the read pulse generation timing.

29. The image pickup device according to claim 28, wherein the function form of said function has a characteristic opposite to the correction for decreasing the distortion aberration of said optical system for the image in said first area and decreasing the distortion aberration for the image in said second area and said correction and control means contracts or enlarges image data corresponding to almost the whole of the image in said second area and outputs the data by reading the image data from said image storage means with said read address.

30. The image pickup device according to claim 24, wherein said correction and control means has a processing information holding section for storing a relative position between the position of each point of an optical image formed by said optical system and the position of an ideally formed optical image as processing information for the image in said first area and storing a displacement value for displacing the position of each point of the optical image formed by said optical system as processing information so as to output image data corresponding to almost the entire optical image formed by said optical system for the image in said second area and corrects and controls at least one of the write operation and read operation of said image storage means in accordance with the processing information stored in the processing information holding section.

31. The image pickup device according to claim 28, wherein the function form of said function is an approximate expression obtained by approximating said distortion aberration by a polynomial of the distance from the center of said first area on the central area of the storage area of said image storage means for the image in said first area.

32. The image pickup device according to claim 28, wherein said correction and control means is able to translate said function in the direction of the generation timing axis of said read pulse in order to decrease correction errors of said distortion aberration due to the inconsistency between the central axis of said optical system and the center of the image pickup surface of said image pickup means.

33. The image pickup device according to claim 28, wherein said correction and control means is able to translate said function in the direction of said read address axis in order to change the positions of a corrected image read out of said image storage means.

34. The image pickup device according to claim 28, wherein said correction and control means is able to multiply said function by any factor in the direction of said read address axis in order to change the magnifications of the corrected image read out of said image storage means.

35. An endoscope system comprising:
an endoscope having an optical system for capturing an optical image of an object arranged at an end of a slender inserting portion and image pickup means for receiving an optical image formed by said optical system, converting the image into electrical picture signals, and outputting the signals;
image storage means for storing said picture signals output from said image pickup means;
read and write control means for controlling read operation and write operation of said image storage means; and
correction and control means constituting said read and write control means to correct and control at least one of the read operation and write operation of said image storage means so as to correct the image in the first area at the central side of said image pickup surface according to a first correction characteristic and the image in the second area at the marginal side of said first area according to a second correction characteristic which is not equivalent to said first correction characteristic, said correction of optical distortion according to said first correction characteristic being performed so that the image in said first area may be enlarged, and said correction according to said second correction characteristic being performed so that the image in said second area may be contracted.

36. The endoscope system according to claim 35, wherein said endoscope is an electronic endoscope in which said image pickup device is arranged at the imaging position of said optical system.

37. The endoscope system according to claim 35, wherein said endoscope is a TV-camera-mounted endoscope comprising an optical endoscope having image transmission means for optically transmitting an optical image formed by said optical system, an imaging optical system mounted on said optical endoscope to form said optical image transmitted by image transmission means, and a TV camera in which said image pickup device is arranged at the imaging position of said imaging optical system.

38. The endoscope system according to claim 35, wherein said correction and control means has a switching section for switching types of corrections for said optical distortion to correct the distortion correspondingly to the type of said optical system of said endoscope.

39. The endoscope system according to claim 38, wherein said correction and control means has a discriminating section for discriminating the type of said optical system of said endoscope and said switching section is switched by the discriminating section and correction is controlled.

40. An image processor for correcting an optical distortion of an image captured by an optical system in accordance with information processing, wherein the optical distortion is changed at the central portion of the image according to a first correction characteristic and the marginal portion of the image according to a second correction characteristic not equivalent to said first correction characteristic, said correction of optical distortion according to said first correction characteristic being performed so that the image of said central portion may be enlarged, and said correction according to said second correction characteristic being performed so that the image at said marginal portion may be contracted.

* * * * *